US005863536A

United States Patent [19]
Jackson et al.

[11] Patent Number: 5,863,536
[45] Date of Patent: *Jan. 26, 1999

[54] PHOSPHORAMIDATE DERIVATIVES

[75] Inventors: Paul F. Jackson, Bel Air; Barbara S. Slusher, Kingsville; Kevin L. Tays, Elkridge; Keith M. Maclin, Baltimore, all of Md.

[73] Assignee: Guilford Pharmaceuticals Inc., Baltimore, Md.

[ * ] Notice: The term of this patent shall not extend beyond the expiration date of Pat. No. 5,804,602.

[21] Appl. No.: 778,733

[22] Filed: Dec. 31, 1996

[51] Int. Cl.$^6$ .................................................. A61K 39/395
[52] U.S. Cl. ........................... 424/130.1; 546/21; 562/10; 514/89; 514/91; 514/95; 514/121
[58] Field of Search ................................. 546/21; 562/10; 574/89, 91, 95, 12, 12.9; 424/130.1, 1.11

[56] References Cited

U.S. PATENT DOCUMENTS

| | | | |
|---|---|---|---|
| 4,151,172 | 4/1979 | Ondetti et al. | 548/413 |
| 4,168,267 | 9/1979 | Petrillo, Jr. | 548/413 |
| 4,316,896 | 2/1982 | Thorsett et al. | 514/80 |
| 4,337,201 | 6/1982 | Petrillo, Jr. | 548/413 |
| 4,374,131 | 2/1983 | Petrillo, Jr. | 514/89 |
| 4,444,765 | 4/1984 | Karanewsky et al. | 514/89 |
| 4,448,772 | 5/1984 | Karanewsky | 514/91 |
| 4,452,790 | 6/1984 | Karanewsky et al. | 514/89 |
| 4,452,791 | 6/1984 | Ryono et al. | 514/79 |
| 4,468,519 | 8/1984 | Krapcho | 548/409 |
| 4,547,324 | 10/1985 | Wong et al. | 562/18 |
| 4,555,506 | 11/1985 | Karanewsky et al. | 514/91 |
| 4,560,680 | 12/1985 | Ryono et al. | 514/82 |
| 4,560,681 | 12/1985 | Karanewsky | 514/82 |
| 4,567,166 | 1/1986 | Karanewsky et al. | 514/82 |
| 4,616,005 | 10/1986 | Karanewsky et al. | 514/80 |
| 4,703,043 | 10/1987 | Karanewsky et al. | 514/80 |
| 4,715,994 | 12/1987 | Parsons et al. | 562/16 |
| 4,716,155 | 12/1987 | Karanewsky et al. | 514/89 |
| 4,849,525 | 7/1989 | Weller, III et al. | 548/413 |
| 4,885,283 | 12/1989 | Broadhurst et al. | 514/78 |
| 4,906,779 | 3/1990 | Weber et al. | 564/238 |
| 4,918,064 | 4/1990 | Cordi et al. | 514/114 |
| 4,959,493 | 9/1990 | Ohfume et al. | 562/506 |
| 4,962,097 | 10/1990 | Parsons et al. | 514/114 |
| 4,988,681 | 1/1991 | Ishikawa et al. | 514/93 |
| 4,994,446 | 2/1991 | Sokolovsky et al. | 514/75 |
| 5,030,732 | 7/1991 | Morita et al. | 548/119 |
| 5,041,644 | 8/1991 | Morita et al. | 564/106 |
| 5,061,806 | 10/1991 | Morita et al. | 548/112 |
| 5,093,525 | 3/1992 | Weber et al. | 564/238 |
| 5,099,063 | 3/1992 | Parsons et al. | 562/16 |
| 5,136,080 | 8/1992 | Miller et al. | 558/410 |
| 5,143,908 | 9/1992 | Parsons et al. | 514/114 |
| 5,145,990 | 9/1992 | Parsons et al. | 562/16 |
| 5,147,867 | 9/1992 | Parsons et al. | 514/114 |
| 5,162,504 | 11/1992 | Horoszewicz | 530/388.2 |
| 5,190,976 | 3/1993 | Weber et al. | 514/634 |
| 5,242,915 | 9/1993 | Ueda et al. | 514/210 |
| 5,262,568 | 11/1993 | Weber et al. | 564/238 |
| 5,326,856 | 7/1994 | Coughlin et al. | 534/14 |
| 5,336,689 | 8/1994 | Weber et al. | 514/634 |
| 5,449,761 | 9/1995 | Belinka, Jr. et al. | 534/10 |
| 5,489,525 | 2/1996 | Paston | 435/7.23 |
| 5,495,042 | 2/1996 | Belinka, Jr. et al. | 562/14 |
| 5,500,420 | 3/1996 | Maiese | 514/131 |
| 5,508,273 | 4/1996 | Beers et al. | 514/141 |
| 5,527,885 | 6/1996 | Coughlin et al. | 534/14 |
| 5,538,866 | 7/1996 | Israeli et al. | 435/69.3 |
| 5,538,957 | 7/1996 | Tsaklakidis et al. | 514/114 |

FOREIGN PATENT DOCUMENTS

96/26272  8/1996  WIPO .

OTHER PUBLICATIONS

Subasinghe, N. et al., "Synthesis of acylis and dehydroaspartic acid analogues of Au–Asp–Glu–OH and their inhibition of rat brain N–acetylated α–linked acidic dipeptidase (NAALA dipeptidase)," *J Med. Chem*, 33 (1990).

Coyle, J. et al., "N–acetyl–aspartyl glutamte," *Excitatory Amino Acids*, (1990).

Tsai, G. et al., "Reductions in acidic amino acids and N–acetylaspartylgutamate in amyotrophic lateral sclerosis," *Brain Research*, 556 (1991).

Tsai, G. et al., "Changes of excitatory neurotransmitter metabolism in schizophrenic brains," *Salmon Lecturer of the New York Academy of Medicine* (Dec. 2–3, 1993).

Stauch, B. et al., "The effects of N–acetylated alpha linked acidic dipeptidase (NAALADase) inhibitors on [$^3$H] NAAG catabolism in vivo," *Neuroscience Letters*, 100 (1989).

Rothstein, J. et al., "Abnormal excitatory amino acid metabolism in amyotrophic lateral sclerosis," *Anals of Neurology*, vol. 28 (1990).

Slusher, B. et al., "Rat brain N–acetylated α–linked acidic dipeptidase activity," *The J. of Biological Chemistry*, vol. 265 (1990).

Myerhoff, J. et al., "Activity of NAAG–hydrolyzing enzyme in brain may effect seizure susceptibility in genetically epilepsy–prone rats," *Molecular Neurobiology of Epilepsy*, (1992).

Slusher, B. et al., "Immunocytochemical localization of the N–acetyl–aspartyl–glutamate (NAAG) hydrolyzing enzyme N–acetylated α–linked acidic dipeptidase (NAALADase)," *J. of Comp. Neurology*, 315 (1992).

Tsai, G. et al., "Immunocytochemical distribution of N–acetylaspartylglutamte in the rat forebrain and glutamatergic pathways," *J. of Chem. Neuroanatomy*, 6 (1993).

Koenig, M. et al., "N–acetyl–asparyl–glutamate (NAAG) elicits rapids increase in intraneuronal $Ca^{2+}$ in vitro," *NeuroReports*, 5 (1994).

(List continued on next page.)

Primary Examiner—Sheela Huff
Attorney, Agent, or Firm—Gary M. Nath; Todd L. Juneau; Nath & Associates

[57] ABSTRACT

The present invention includes phosphoramidate derivatives, compositions containing the same, and methods of using them as NAALADase inhibitors, particularly for the treatment of glutamate abnormalities and associated nervous tissue insult in a animal and for treatment of prostate disease and prostate cancer by inhibition of NAALADase enzyme.

24 Claims, 7 Drawing Sheets

OTHER PUBLICATIONS

Jackson, P. et al., "Design, synthesis, and biological acitivity of a potent inhibitor of the neuropeptidase N–acetylated α–linked acidic dipeptidase," *J. of Medicinal Chemistry*, (1995).

Woods, D. et al., "Gender–linked injury after focal ischemia," *Soc. for Neuroscience 1996 Abstract Form*, (1996).

Slusher, B. et al., "NAALADase: a potential regulator of synaptic glutamate," *Biotech Update DuPont NEN*, 9 (1994).

Myerhoff, J. et al., "Genetically epilepsy–prone rats have increased brain regional activity of an enzyme which liberates glutamate from N–acetyl–aspartyl–glutamate," *Brain Research*, 593 (1992).

Vornov, J. et al., "Toxic NMDA–receptor activation occurs during recovery in a tissue culture model of ischemia," *J. of Neurochemistry*, 65 (1995).

Carter, R. et al., "Prostate–specific membrane antigen is a hydrolase with substrate and pharmacologic characteristics of neuropeptidase," *Proc. Nat. Acad. Sci.*, 93 (1996).

Bhardwaj, A. et al., "Striatal nitric oxide (NO) production is enhanced in focal cerebral ischemia: an in vivo microdialysis study," *Soc. for Neuroscience 1996 Abstract Form*, (1996).

Heston, W.D.W., "Potential Uses of Prostate Specific Membrane Antigen (PMSA): a Neurocarboxypeptidase and Membrane Folate Hydrolase," *Urologe [A]*, v. 35, pp. 400–407 (1996).

Cecil Textbook of Medicine, 19th edition pp. 2076–2077, 1992.

Osband et al, Immunology Today. vol. 11 p. 193, 1990.

Johnson et al, Cancer Treatment Reviews vol. 2 p. 1, 1975.

Barinaga, Science vol. 264 p. 772, May 1994.

Bioworld Today vol. 5 pp. 1–2, Jun. 1994.

PHOSPHORAMIDATE DERIVATIVES

BACKGROUND OF THE INVENTION

1. Field of the Invention

The present invention relates to novel compounds and compositions which inhibit N-Acetylated α-Linked Acidic Dipeptidase (NAALADase) enzyme activity, and in particular to phosphoramidate derivatives and compositions containing the same which inhibit NAALADase enzyme activity in humans and warm-blooded animals. The present invention is also directed to novel compounds and compositions which inhibit NAALADase enzyme activity and are useful as novel agents for treatment of glutamate abnormalities in animals, particularly the prevention or alleviation of brain damage caused by strokes and other types of ischemic damage. Furthermore, the present invention is also directed to novel compounds and compositions useful as novel agents for treatment of cancer and related diseases of the prostate, particularly prostate cancer.

2. Description of the Prior Art

Ischemia

Ischemia, a localized tissue anemia resulting from the obstruction of the inflow of arterial blood, can cause extensive damage when it occurs in the brain or central nervous system. Central nervous tissue, and to a lesser extent peripheral nervous tissue, has poor reparative abilities. Thus damage to nervous tissue causes significant permanent disability and is a frequent cause of death. Damage to nervous tissue may occur in many ways, not only through ischemia in cerebrovascular accidents, but also in cerebral circulatory disturbances, episodes of absolute and relative hypoxia, metabolic disturbances and various forms of trauma.

Global ischemia occurs under conditions in which blood flow to the entire brain ceases for a period of time, such as may result from cardiac arrest. Focal ischemia occurs under conditions in which a portion of the brain is deprived of its normal blood supply, such as may result from thromboembolytic occlusion of a cerebral vessel, traumatic head injury, edema, and brain tumors. In areas of focal ischemia or damage, there is a core of more profound damage, surrounded by a perifocal penumbra of lesser damage. This is because the neurons in the penumbra can for a time maintain homeostasis thus rendering them potentially more salvageable by pharmacological agents.

Both global and focal ischemic conditions have the potential for producing widespread neuronal damage, even if the ischemic condition is transient. Although some permanent neuronal injury may occur in the initial mixture following cessation of blood flow to the brain, the damage in global and focal ischemia occurs over hours or even days following the ischemic onset. Much of this neuronal damage is attributed to glutamate toxicity and secondary consequences of reperfusion of the tissue, such as the release of vasoactive products by damaged endothelium, and the release by the damaged tissues of cytotoxic products including free radicals, leukotrienes, and the like.

Glutamate neurotoxicity, which is a major factor in ischemic neuronal injury, appears to begin with resumption of oxidative metabolism and thus occurs both during reversible ischemia and during recovery. Many attempts have been made to avoid this problem by blocking of the various receptors including NMDA receptors, AMPA receptors, Kainate receptors, and MGR receptors, which are stimulated by glutamate and are also strongly involved in nerve cell death occurring after the onset of global or focal ischemia. When ischemia occurs, such as during a stroke or heart attack, there is an excessive release of endogenous glutamate, resulting in the overstimulation of NMDA receptors, AMPA receptors, Kainate receptors, and MGR receptors. Interaction of the glutamate with these receptors causes the ion channel associated with these receptors to open, allowing a flow of cations across the cell membrane. This flux of ions, particularly $Ca^{2+}$ into the cells, plays an important role in nerve cell death.

Much activity has been undertaken in attempting to prevent glutamate from exciting these receptors. This has proven difficult since these receptors each have many different sites to which the glutamate may bind. Furthermore, many of the compositions that are effective in blocking glutamate from these receptors have also proven in clinical trials to be toxic to the animal that they are administered to.

Currently there is no known effective treatment for nervous tissue damage. At best, supportive measures may be taken in a hospital during the period after nervous tissue insult, such as stroke or trauma. Several drug strategies that have been proposed for treatment of stroke and other neuronal conditions related to ischemia have met with differing and incomplete success as agents to protect the nervous system from damage. Anti-coagulants, such as heparin, have been examined, but with mixed results. Similarly, antivasoconstriction agents, such as flunarazine, excitatory neurotransmitter antagonists, such as MK-801 and AP7, and anti-edemic compounds have shown mixed results, with no clear benefits to outweigh a variety of side effects, including neurotoxicity or increased susceptibility to infection. Nimodipine, a calcium channel blocker, is used clinically to treat vasospasm after subarachnoid hemorrhage. Methylprednisolone, a steroid, in very high doses is helpful in spinal cord compression. Tirilazad, a 21-aminosteroid linked to a free radical scavenger, underwent clinical trials to decrease the damage caused by stroke.

The high rate of disability from nervous insults demonstrates the need for an effective neuroprotective agent. Unfortunately, drugs which have been proposed to date for the treatment of stroke and other ischemic-related conditions of the brain are either (i) relatively ineffective, (ii) effective only at dosage levels where undesired side effects are observed, (iii) produce systemic effects, such as hypotension, which comprise the potential effectiveness of the drug, and/or (iv) are toxic to the patient.

Glutamate Toxicity Within the Central Nervous System

Efforts to examine the role of glutamate toxicity in diseases of the brain, i.e. epilepsy, amyotrophic lateral sclerosis (ALS), schizophrenia, and Alzheimer's disease, led researchers in an attempt to ascertain the exact role of N-acetylated α-linked acidic dipeptidase (NAALADase) and N-acetyl-L-aspartate-L-glutamate (NAAG) in the central nervous system (CNS).

The dipeptide NAAG is an abundant nervous system specific peptide which is present in synaptic vesicles and released upon neuronal stimulation in several systems. As a major peptidic component of the brain, NAAG is present in levels comparable to that of the major inhibitory neurotransmitter γ-aminobutyric acid (GABA). Although NAAG was first isolated in 1964, there was little activity toward elucidating its role in the CNS until the deleterious nature of excess glutamate in a variety of disease states became apparent. Due to its structural similarity to glutamate, NAAG has been suggested to have a variety of roles similar to those of glutamate itself, including functioning as a neurotransmitter or a cotransmitter, neuromodulator, or as a precursor of the neurotransmitter glutamate. NAAG has elicited excitatory responses both in vitro and in vivo, but is significantly less potent than glutamate.

Prostate Cancer

In a separate area of research, prostate cancer has been determined to now be the leading form of cancer among men and the second most frequent cause of death from cancer in men. It is estimated that more than 165,000 new cases of prostate cancer were diagnosed in 1993, and more than 35,000 men died from prostate cancer in that year. Additionally, the incidence of prostate cancer has increased by 50% since 1981, and mortality from this disease has continued to increase. Previously, most men died of other illnesses or diseases before dying from their prostate cancer. We now face increasing morbidity from prostate cancer as men live longer and the disease has the opportunity to progress.

Current therapies for prostate cancer focus exclusively upon reducing levels of dihydrotestosterone to decrease or prevent growth of prostate cancer. In addition to the use of digital rectal examination and transrectal ultrasonography, prostate-specific antigen (PSA) concentration is frequently used in the diagnosis of prostate cancer.

Prostate Specific Antigen (PSA) is a well known prostate cancer marker. PSA is a protein produced by prostate cells and is frequently present at elevated levels in the blood of men who have prostate cancer. PSA has been shown to correlate with tumor burden, serve as an indicator of metastatic involvement, and provide a parameter for following the response to surgery, irradiation, and androgen replacement therapy in prostate cancer patients. It should be noted that Prostate Specific Antigen (PSA) is a completely different protein from Prostate Specific Membrane Antigen (PSMA). Although they have similar nomenclature, the two proteins have different structures and functions.

Prostate Specific Membrane Antigen (PSMA)

In 1993, the molecular cloning of a prostate-specific membrane antigen (PSMA) was reported as a potential prostate carcinoma marker and hypothesized to serve as a target for imaging and cytotoxic treatment modalities for prostate cancer. Antibodies against PSMA have been described and examined clinically for diagnosis and treatment of prostate cancer. In particular, Indium-111 labelled PSMA antibodies have been described and examined for diagnosis of prostate cancer and itrium-labelled PSMA antibodies have been described and examined for the treatment of prostate cancer.

PSMA is expressed in prostatic ductal epithelium and is present in seminal plasma, prostatic fluid and urine. In 1996, it was found that the expression of PSMA cDNA actually confers the activity of NAALADase. This is entirely unexpected because until recently NAALADase research has been limited to its role in the brain and its effect on neurotransmitters whereas PSMA has been described and examined for the diagnosis and therapy of prostate cancer.

NAALADase

In 1988, a brain enzyme, NAALADase, was identified which hydrolyzes NAAG to N-acetylaspartate (NAA) and glutamate (See TABLE I, below).

Catabolism of NAAG by the peptidase NAALADase.

TABLE 1

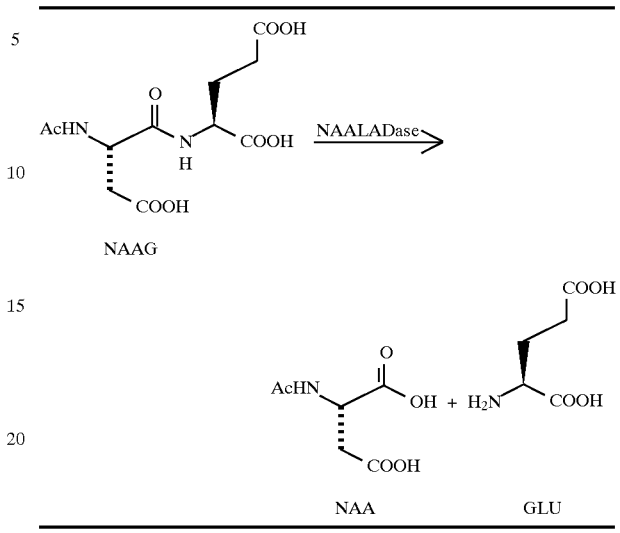

NAALADase, which derives its name from its structural specificity for N-acetylated acidic dipeptides, is a membrane-bound metallopeptidase having a denatured molecular mass of 94 kDa, that catabolizes NAAG to N-acetylaspartate (NAA) and glutamate. It has been demonstrated that [$^3$H]NAAG is degraded in vivo by an enzyme with the pharmacological characteristics of NAALADase, which supports a role for NAALADase in the metabolism of endogenous NAAG.

Rat NAALADase activity has been extensively characterized and demonstrates a high affinity for hydrolysis of its putative substrate NAAG, with a Km=140 nM. Recently, NAALADase also has been shown to cleave the non-acetylated peptide, aspartylglutamate, with high affinity. Research has also found that the enzyme is membrane-bound, stimulated by chloride ions, and inhibited by polyvalent cation chelators, suggesting that it is a metallopeptidase.

In mammals, NAALADase is enriched in synaptic plasma membranes and is primarily localized to neural tissue and the kidneys. NAALADase has not been found in large quantities in the mammalian liver, heart, pancreas, or spleen.

Examination of NAAG and NAALADase has been conducted for several different human and animal pathological conditions. It has been demonstrated that intra-hippocampal injections of NAAG elicit prolonged seizure activity. More recently, it was reported that rats genetically prone to epileptic seizures have a persistent increase in their basal level of NAALADase activity. These observations are consistent with the hypothesis that increased availability of synaptic glutamate elevates seizure susceptibility, and suggest that NAALADase inhibitors may provide anti-epileptic activity.

NAAG and NAALADase have also been implicated in the pathogenesis of ALS and in the pathologically similar animal disease called Hereditary Canine Spinal Muscular Atrophy (HCSMA). It has been shown that concentrations of NAAG and its metabolites—NAA, glutamate and aspartate—are elevated two- to three-fold in the cerebrospinal fluid of ALS patients and HCSMA dogs.

In addition, NAALADase activity is significantly increased (two- to three-fold) in post-mortem spinal cord tissue from ALS patients and HCSMA dogs. Although highly speculative, NAALADase inhibitors may be clinically useful in curbing the progression of ALS if increased metabolism of NAAG is responsible for the alterations of CSF levels of these acidic amino acids and peptides. Abnormalities in NAAG levels and NAALADase activity have also been documented in post-mortem schizophrenic brain, specifically in the prefrontal and limbic brain regions, underscoring the importance of examining the metabolism of NAAG in the pathophysiology of schizophrenia.

The identification and purification of NAALADase led to the proposal of another role for NAAG: specifically that the dipeptide may serve as a storage form of synaptic glutamate.

NAALADase Inhibitors

Only a few NAALADase inhibitors have been identified in the prior art thus far and those that have been identified have only been used in non-clinical neurological research. Examples of such inhibitors include general metallopeptidase inhibitors such as o-phenanthrolene, metal chelators such as EGTA and EDTA, and peptide analogs such as quisqualic acid and beta-NAAG. It should be noted that prior to the compositions of the present invention, NAALADase inhibitors have either had toxic side effects or were not capable of being administered in pharmaceutically effective amounts.

SUMMARY OF THE INVENTION

The present invention is directed to novel compounds and compositions which inhibit N-Acetylated α-Linked Acidic Dipeptidase (NAALADase) enzyme activity, and in particular to phosphoramidate derivatives and compositions containing the same which inhibit NAALADase enzyme activity in humans and warm-blooded animals. The present invention is also directed to novel compounds and compositions which inhibit NAALADase enzyme activity and are useful as novel agents for treatment of glutamate abnormalities in animals, particularly the prevention or alleviation of brain damage caused by strokes and other types of ischemic damage.

The present invention is also directed to the surprising discovery that NAALADase inhibitors exhibit a significant inhibitory effect on the growth of cancer cells, and particularly prostate cancer cells. The present disclosure relates to novel compositions containing dipeptidase inhibitors, and more particularly, to compounds and compositions which inhibit N-Acetylated α-Linked Acidic Dipeptidase (NAALADase) enzyme activity useful for treatment for diseases of the prostate, particularly, prostate cancer. Furthermore, as has been found in other tissues of the body, NAALADase inhibitors may show efficacy in the treatment of other forms of cancer.

The present invention is based upon the surprising discovery that the NAALADase inhibitors of the present invention exhibit increased potency over prior art compounds.

Preferred compositions of the present invention include compounds having the following formula:

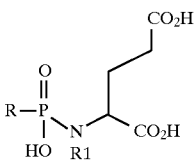

where
R and R1 are independently hydrogen, $C_1$–$C_9$ straight or branched chain alkyl or alkenyl group, $C_3$–$C_8$ cycloalkyl, $C_3$ or $C_5$ cycloalkyl, $C_5$–$C_7$ cycloalkenyl, or $Ar_1$.

The present invention also contemplates the use of said alkyl, alkenyl, cycloalkyl, cycloalkenyl or aryl groups to be optionally substituted with $C_3$–$C_8$ cycloalkyl, $C_3$ or $C_5$ cycloalkyl, $C_5$–$C_7$ cycloalkenyl, $C_1$–$C_4$ alkyl, $C_1$–$C_4$ alkenyl, hydroxy, halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, amino, or $Ar_1$, and where $Ar_1$ is selected from the group consisting of 1-napthyl, 2-napthyl, 2-indolyl, 3-indolyl, 2-furyl, 3-furyl, 2-thienyl, 3-thienyl, 2-, 3-, or 4-pyridyl, or phenyl, having one to three substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, benzyloxy, and amino; or pharmaceutically acceptable salts or hydrates thereof.

Especially preferred compounds of the present invention are selected from the group consisting of:
N-[Methylhydroxyphosphinyl]glutamic Acid;
N-[Ethylhydroxyphosphinyl]glutamic Acid;
N-[Propylhydroxyphosphinyl]glutamic Acid;
N-[Butylhydroxyphosphinyl]glutamic Acid;
N-[Phenylhydroxyphosphinyl]glutamic Acid;
N-[(Phenylmethyl)hydroxyphosphinyl]glutamic Acid;
N-[((2-Phenylethyl)methyl)hydroxyphosphinyl]glutamic Acid; and
N-Methyl-N-[Phenylhydroxyphosphinyl]glutamic Acid.

Compounds of the present invention which are highly preferred are selected from the group consisting of:
N-[Propylhydroxyphosphinyl]glutamic Acid;
N-[Butylhydroxyphosphinyl]glutamic Acid;
N-[Phenylhydroxyphosphinyl]glutamic Acid; and
N-[(Phenylmethyl)hydroxyphosphinyl]glutamic Acid.

Compositions within the scope of the present invention contain the above described compounds and are formulated with a suitable pharmaceutical carrier. Such carriers are especially formulated in order to best utilize the compound for the particular treatment, such as for treating glutamate abnormalities in an animal, treating nervous insult as defined herein, treating ischemia in an animal, treatment using the compounds of the present invention as glutamate modulators, treatment to provide recovery of tissues after an ischemic event, and treatment to decrease injuries caused by ischemia such as brain injuries caused by global ischemia or focal ischemia.

Further preferred embodiments include the use of additional therapeutic agents useful for treating ischemia. The agent can also include any pharmaceutical compound useful for the treatments described herein to be delivered in combination with the compounds and compositions of the present invention.

Compositions within the scope of the present invention also are formulated with a suitable pharmaceutical carrier in order to best utilize the compound for inhibition of tumor growth, inhibition of tumor cell growth, and inhibition of NAALADase enzyme activity. A particularly preferred tumor type is prostatic adenocarcinoma.

Yet another preferred embodiment is directed to a composition for treating prostate diseases selected from the group consisting of prostate cancer and benign prostatic hyperplasia in an animal, which comprises: (i) the compound described above and (ii) a pharmaceutically acceptable carrier for administering said compound to said animal.

Further preferred embodiments include the use of additional therapeutic agents useful for treating diseases of the prostate. Such agents may be selected from the group consisting of: therapeutic hormones, chemotherapeutic agents, monoclonal antibodies, anti-angiogenesis agents, and radiolabelled compounds. The agent can also include any pharmaceutical compound useful for the treatments described herein to be delivered in combination with the compounds and compositions of the present invention.

The methods of the present invention include using the compounds of the present invention and/or compositions containing phosphoramidate derivatives that inhibit NAALADase enzyme activity which have been found useful for the treatment of NAALADase related indications. Especially preferred indication include treating glutamate abnormalities in an animal, treating nervous insult as defined herein, treating ischemia in an animal, treatment using the compounds of the present invention as glutamate modulators, treatment to provide recovery of tissues after an ischemic event, and treatment to decrease injuries caused by ischemia such as brain injuries caused by global ischemia or focal ischemia. It is contemplated that these methods can also utilize additional therapeutic agents useful for treating nerve-related indications such as ischemia. Such additional agents are known to persons of ordinary skill in the art.

Further preferred methods of the present invention include treatment using the compounds and compositions described herein for inhibition of tumor growth, inhibition of tumor cell growth, and inhibition of NAALADase enzyme activity. A particularly preferred tumor type is prostatic adenocarcinoma.

Additional preferred embodiments are directed to compounds and compositions for treating prostate diseases selected from the group consisting of prostate cancer and benign prostatic hyperplasia in an animal.

BRIEF DESCRIPTION OF THE FIGURES

FIG. 6 shows the effect of 7-day treatment with quisqualate on the growth of LNCAP cells. Concentrations ranging from 10 nM to 1 $\mu$M of quisqualate show a sharp dose-dependent decrease of LNCAP cell proliferation as indicated by the significant decrease in the incorporation of [3H]thymidine.

FIG. 7 shows the effect of 7-day treatment with 2-(phosphonomethyl) pentanedioic acid on the growth of LNCAP cells. Concentrations ranging from 100 pM to 10 nM of 2-(phosphonomethyl)pentanedioic acid show a sharp dose-dependent decrease of LNCAP cell proliferation as indicated by the significant decrease in the incorporation of [3H] thymidine.

DETAILED DESCRIPTION OF THE INVENTION

Figure 1:
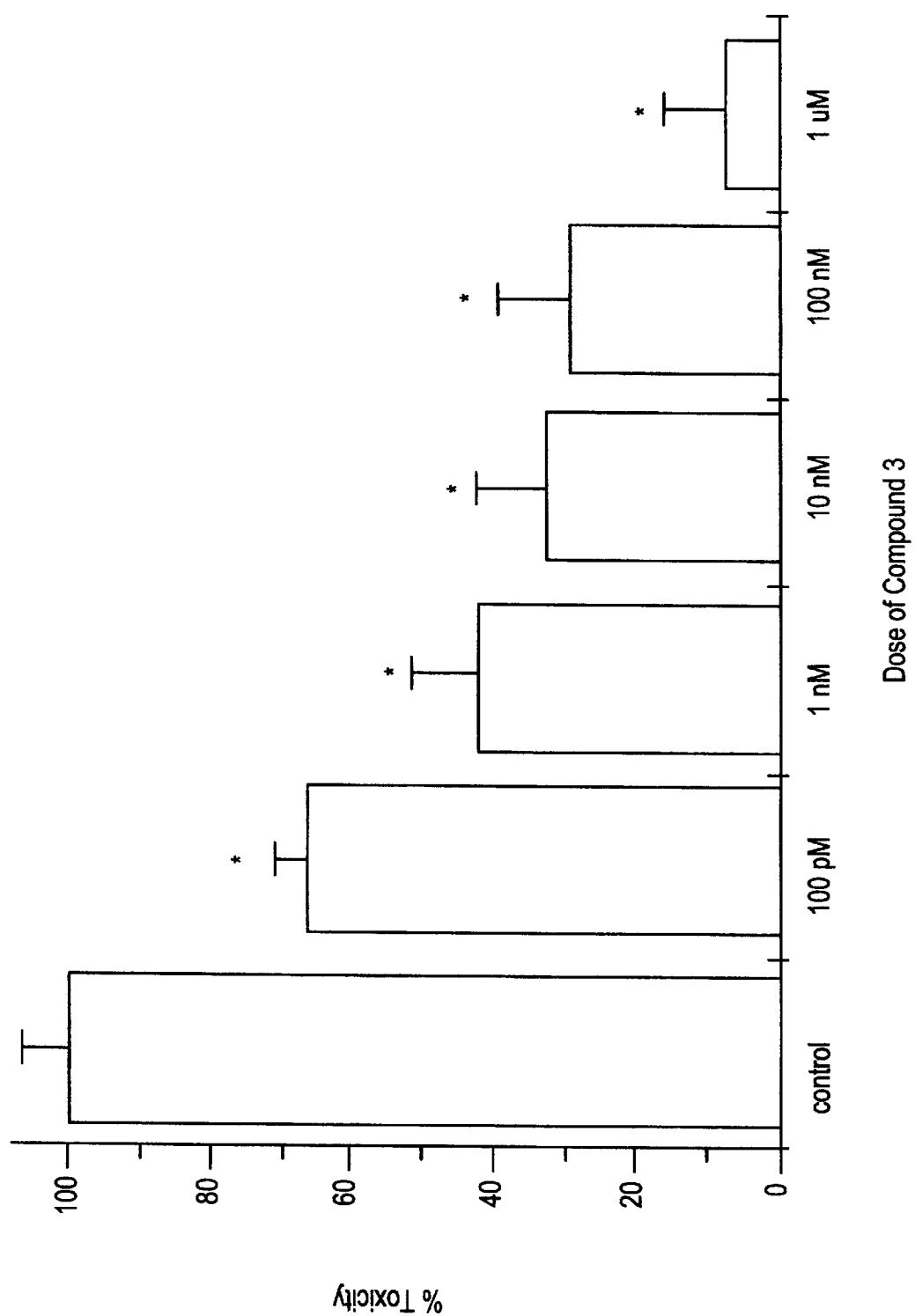
FIG. 1 is a bar graph plotting the in vitro toxicity of ischemic insult (cyanide and 2 deoxy glucose) measured in cortical cultures in the presence of various dosages of 2-(Phosphonomethyl)pentanedioic Acid.

The present invention is directed to novel NAALADase inhibitors. The compounds of the present invention also exhibit increased potency due to their novel structures. The compounds of the present invention are useful for treating ischemia, in particular global and focal ischemia, in humans and warm-blooded animals.

Furthermore, the compounds of the present invention include phosphoramidate derivatives that inhibit NAALADase enzyme activity and which have been found useful for inhibiting the growth of prostate cancer cells. Although the use of NAALADase inhibitors is exemplified for the treatment of prostate cancer, compositions including NAALADase inhibitors are not limited to this specific form as cancer. NAALADase has been found in other tissues in the body, which results in efficacy in the treatment of other forms of cancer. For example, the kidney, brain, and testis have NAALADase present. As a result, in these examples brain cancer, kidney cancer, or testicular cancer may be treated via this approach. Other tissues will correlate with other treatments accordingly.

NAALADase is an enzyme which is a membrane-bound metalloprotease that hydrolyzes the dipeptide, N-acetyl-L-aspartate-L-glutamate (NAAG) to yield glutamate and N-acetylaspartate. The amino acid L-glutamate is a neurotransmitter that mediates fast neuronal excitation in a majority of synapses in the central nervous system (CNS). Once released into the synapse, L-glutamate can stimulate the N-methyl-D-aspartate (NMDA) receptor, a subtype of an excitatory amino acid receptor. It has been discovered that excessive activation of the NMDA receptor has been implicated in a variety of acute as well as chronic neurophatholgical processes such as ischemia, epilepsy and Huntington's disease. Thus, considerable effort has focused on finding novel therapeutic agents to antagonize the postsynaptic effects of L-glutamate mediated through the NMDA receptor. Although not limited to any one particular theory, it is believed that the compounds of the present invention modulate levels of glutamate by acting on a storage form of glutamate which is hypothesized to be upstream from the effects mediated by the the NMDA receptor.

Preferred compositions of the present invention include compounds having the following formula:

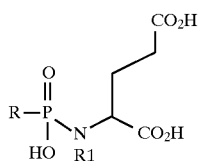

where

R and R1 are independently hydrogen, $C_1$–$C_9$ straight or branched chain alkyl or alkenyl group, $C_3$–$C_8$ cycloalkyl, $C_3$ or $C_5$ cycloalkyl, $C_5$–$C_7$ cycloalkenyl, or $Ar_1$.

The present invention also contemplates compounds wherein said alkyl, alkenyl, cycloalkyl, cycloalkenyl, or aryl groups to be optionally substituted with $C_3$–$C_8$ cycloalkyl, $C_3$ or $C_5$ cycloalkyl, $C_5$–$C_7$ cycloalkenyl, $C_1$–$C_4$ alkyl, $C_1$–$C_4$ alkenyl, hydroxy, halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, amino, or $Ar_1$, and where $Ar_1$ is selected from the group consisting of 1-napthyl, 2-napthyl, 2-indolyl, 3-indolyl, 2-furyl, 3-furyl, 2-thienyl, 3-thienyl, 2-, 3-, or 4-pyridyl, or phenyl, having one to three substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, benzyloxy, and amino; or pharmaceutically acceptable salts or hydrates thereof.

It has been unexpectedly found that the right hand side of the molecular structure depicted above is necessary for substrate recognition by NAALADase enzyme. Thus, the present invention only contemplates substitutions to the left hand side and at the nitrogen, indicated by the R and R1 group, of the phosphoramidate derivative structure above.

DEFINITIONS

"NAALADase" as used herein refers to N-Acetylated Alpha-Linked Acidic Dipeptidase. The enzyme was originally named for it's substrate specificity for hydrolyzing N-acetylated alpha-linked acidic dipeptides. Currently, it is known that the enzyme has a broader range of substrate specificity than originally discovered, particularly that the enzyme does not require N-acetylation or alpha-linkage. Thus, as used herein "NAALADase" encompasses other names used in the literature such as NAAG hydrolyzing enzyme and NAALA dipeptidase.

As used in the specification and claims, the chemical structures refer to conventional designations. For example, "alkyl" is a paraffinic hydrocarbon group which may be derived from an alkane by dropping one hydrogen from the formula, such as methyl, ethyl, propyl, isopropyl, butyl, and so forth. "Alkenyl" is an olefinic unsaturated hydrocarbon having one or more double bonds such as methylene, ethylene, propylene, isopropylene, butylene, and so forth. The term "Cyclo", used herein as a prefix, refers to a structure characterized by a closed ring. The term "oxy", used herein as a suffix, i.e. alkoxy, alkenoxy, phenoxy, and so forth, refers to having one or more oxygen molecules attached. Thus, the term "carboxy" may describe, for example, a carbon having both an oxygen and a hydroxy moiety attached.

"Halogen" includes bromo, fluoro, chloro and iodo; "halomethyl" includes mono-, di-, and tri-halo groups including trifluoromethyl; amino compounds include amine ($NH_2$) as well as substituted amino groups comprising alkyls of one through six carbons; "$Ar_1$", chemical shorthand for "aryl", includes aromatic ring compounds such as benzene, phenyl, naphthyl, indolyl, furyl, thienyl, pyridyl, and substituted forms thereof; "aralkyl", is an aryl being attached through an alkyl chain, straight or branched, of from one through six carbons such as phenylpropyl group.

The term "inhibition", in the context of enzyme inhibition, relates to reversible enzyme inhibition such as competitive, uncompetitive, and noncompetitive inhibition. This can be experimentally distinguished by the effects of the inhibitor on the reaction kinetics of the enzyme, which may be analyzed in terms of the basic Michaelis-Menten rate equation. Competitive inhibition occurs when the inhibitor can combine with the free enzyme in such a way that it competes with the normal substrate for binding at the active site. A competitive inhibitor reacts reversibly with the enzyme to form an enzyme-inhibitor complex [EI], analogous to the enzyme-substrate complex:

$$E + I = EI$$

Following the Michaelis-Menten formalism, we can define the inhibitor constant, $K_i$, as the dissociation constant of the enzyme-inhibitor complex:

$$K_i = \frac{[E][I]}{[EI]}$$

Thus, in accordance with the above and as used herein, $K_i$ is essentially a measurement of affinity between a molecule, and its receptor, or in relation to the present invention, between the present inventive compounds and the enzyme to be inhibited. It should be noted that IC50 is a related term used when defining the concentration or amount of a compound which is required to cause a 50% inhibition of the target enzyme.

The term "inhibition", in the context of tumor growth or tumor cell growth, may be assessed by delayed appearance of primary or secondary tumors, slowed development of primary or secondary tumors, decreased occurrence of primary or secondary tumors, slowed or decreased severity of secondary effects of disease, arrested tumor growth and regression of tumors, among others. In the extreme, complete inhibition, is referred to herein as prevention.

The term "prevention", in relation to tumor growth or tumor cell growth, means no tumor or tumor cell growth if none had occurred, no further tumor or tumor cell growth if there had already been growth.

The term "prostate disease" relates to prostate cancer such as adenocarcinoma or metastatic cancers, conditions characterized by abnormal growth of prostatic epithelial cells such as benign prostatic hyperplasia, and other conditions requiring treatment by the compounds of the present invention.

The compounds and compositions of the present invention useful for treatment of cancer, include but are not limited to types of cancer selected from the following group: ACTH-producing tumors, acute lymphocytic leukemia, acute nonlymphocytic leukemia, cancer of the adrenal cortex, bladder cancer, brain cancer, breast cancer, cervix cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head & neck cancer, Hodgkin's lymphoma, Kaposi's sarcoma, kidney cancer, liver cancer, lung cancer(small and/or non-small cell), malignant peritoneal effusion, malignant pleural effusion, melanoma, mesothelioma, multiple myeloma, neuroblastoma, non-Hodgkin's lymphoma, osteosarcoma, ovary cancer, ovary (germ cell) cancer, pancreatic cancer, penis cancer, prostate cancer, retinoblastoma, skin cancer, soft-tissue sarcoma, squamous cell carcinomas, stomach cancer, testicular cancer, thyroid cancer, trophoblastic neoplasms, cancer of the uterus, vaginal cancer, cancer of the vulva, and Wilm's tumor.

The term "ischemia" relates to localized tissue anemia due to obstruction of the inflow of arterial blood. Global ischemia occurs under conditions in which blood flow to the entire brain ceases for a period of time, such as may result from cardiac arrest. Focal ischemia occurs under conditions in which a portion of the brain is deprived of its normal blood supply, such as may result from thromboembolytic occlusion of a cerebral vessel, traumatic head injury, edema, and brain tumors.

The term "nervous tissue" refers to the various components that make up the nervous system including neurons, neural support cells, glia, Schwann cells, vasculature contained within and supplying these structures, the central nervous system, the brain, the brain stem, the spinal cord, the junction of the central nervous system with the peripheral nervous system, the peripheral nervous system and allied structures.

The term "nervous function" refers to the various functions of the nervous system and its parts which are manifest in sensing the environment, awareness of it, homeostasis to it and interaction with it as shown, by example, in the ability to perform activities of daily living, work, cogitation and speech.

The term "nervous insult" refers to damage to nervous tissue which includes brain and nervous tissue damage and destruction, in whole or in part, and resultant morbidity, disability, neurologic deficia and death. Nervous insult can be from various origins including ischemia, hypoxia, cerebrovascular accident, metabolic, toxic, neurotoxic, trauma, surgery, iatrogenic, pressure, mass effect, hemorrhage, thermal, chemical, radiation, vasospasm, neurodegenerative disease, neurodegenerative process, infection, Parkinson's disease, amyotrophic lateral sclerosis, myelination/demyelination processes, epilepsy, cognitive disorders, glutamate abnormalities, and their secondary effects.

The term "glutamate abnormalities" refers to any condition, disease, or disorder that involves glutamate, and includes but is not limited to the nervous insults listed above.

The term "glutamate modulator" refers to any composition of matter, alone or in combination with another agent, which affects the level of glutamate in an animal, including a human being.

The term "neuroprotective" is an effect which reduces, arrests, or ameliorates nervous insult and is protective, resuscitative or revivative for nervous tissue that has suffered nervous insult.

The term "treatment" refers to any process, action, application, therapy, or the like, wherein an animal, including a human being, is subject to medical aid with the object of improving the animal's condition, directly or indirectly.

The term "Compound 3" refers to the compound 2-(Phosphonomethyl)pentanedioic Acid.

Synthesis of NAALADase Inhibitors

It has been unexpectedly found that compounds with the following general structure were found to be very potent inhibitors of NAALADase:

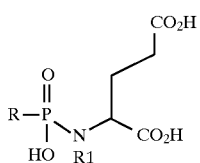

These compounds may be prepared by the general method of Ji et al., *Synthesis*, 1988, 444–448. Their synthesis is outlined in Schemes 1, 2, and 3 below.

All of the above-described inhibitors can be synthesized by standard organic synthetic procedures. The precursor compounds of the present invention can be easily made by a ordinary person skill in the art utilizing known methods, such as Scheme 1 below. Production of compounds containing the R group substitutions can be easily made utilizing known methods. See, for example, Froestl et al., J. Med. Chem., 1995, 38, 3313–3331, Phosphinic Acid Analogues of GABA.

Scheme 1

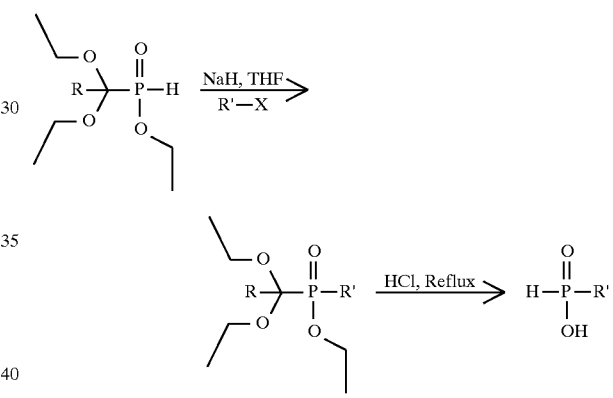

Further methods of synthesizing phosphinic acid esters are also described in *J. Med. Chem.*, 1988, 31, 204–212, and may be found in Scheme II, below.

Scheme II

Method A

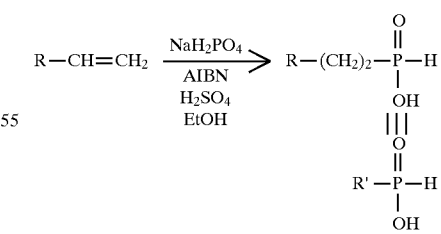

| | | | |
|---|---|---|---|
| A. R' = | (CH$_2$)$_3$Ph | H. | n-C$_7$H$_{15}$ |
| B. | (CH$_2$)$_4$Ph | I. | n-C$_8$H$_{17}$ |
| C. | (CH$_2$)$_5$Ph | J. | n-C$_9$H$_{19}$ |
| D. | (CH$_2$)$_4$(P—F—Ph) | K. | n-C$_{10}$H$_{21}$ |
| E. | (CH$_2$)$_4$(3-pyridyl) | L. | CH$_2$(CH)(CH$_3$)C$_4$H$_9$ |
| F. | n-C$_5$H$_{11}$ | M. | CH$_2$(CH$_3$)CH(CH$_3$)$_2$ |
| G. | n-C$_6$H$_{13}$ | | |

13
-continued
Scheme II

Method B

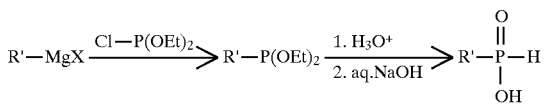

N. R' = n-C$_4$H$_9$
O. CH(CH$_3$)C$_5$H$_{11}$

Starting with the aforementioned phosphinic acid esters, there are a variety of routes that can be used to prepare the compounds of the present invention. For example, a general route was recently described in Ji et al., *Synthesis*, 1988, 444–448, and is set forth below in Scheme III.

SCHEME III

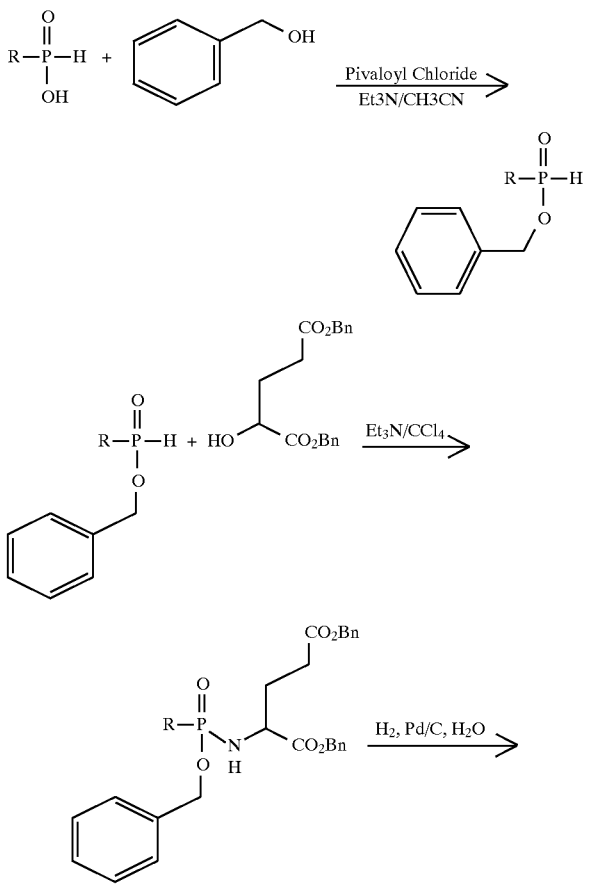

In Vitro Inhibition of NAALADase Activity

Three compounds were tested for inhibition of NAALADase activity: 2-(phosphonomethyl) pentanedioic acid, 2-(phosphonomethyl)succinic acid, and 2-[[2-carboxyethyl) hydroxyphosphinol]methyl]-pentanedoic acid. The results are shown in Table II.

14

TABLE II in vitro Activity of NAALADase Inhibitors

| compd | K$_i$ (nM) |
|---|---|
| 2-(phosphonomethyl)pentanedioic acid | 0.275 ± 0.08 |
| 2-(phosphonomethyl)succinic acid | 700. ± 67.3 |
| 2-[[2-carboxyethyl)hydroxyphosphinol] methyl]-pentanedoic acid) | 1.89 ± 0.19 |

2-(phosphonomethyl)pentanedioic acid showed a high level of NAALADase inhibiting activity, with a K$_i$ of 0.27 nM (Table II). The activity of this compound is >1000 times more potent than that of previously described inhibitors. The procedure for assaying the compounds is set forth below.

NAALADase activity was assayed as described. In brief, the assay measured the amount of [$^3$H]Glu liberated from [$^3$H]NAAG in 50 mM Tris-Cl buffer in 15 min at 37° C. using 30–50 μg of synaptosomal protein; substrate and product were resolved by anion-exchange liquid chromatography. Duplicate assays were always performed so that no more than 20% of the NAAG was digested, representing the linear range of peptidase activity. Quisqualate (100 μM) was included in parallel assay tubes to confirm the specificity of measurements.

The 2-(phosphonomethyl)succinic acid showed a large decrease in efficacy in inhibiting the activity of NAALADase (Table II), suggesting that a glutamate analog attached to the phosphonic acid is required for potent inhibition of the enzyme. In addition, 2-[[2-carboxyethyl) hydroxyphosphinol]methyl]-pentanedoic acid, which has an additional carboxylic acid side chain similar to the aspartate residue found in NAAG, did not lead to an increase in potency.

TOXICOLOGICAL EFFECTS

The compounds of the present invention have demonstrated that they are non-toxic when administered to rats and mice during in vivo neurological experiments and would accordingly, not be expected to demonstrate toxic effects in humans when administered in therapeutic doses. Furthermore, NAALADase inhibitors have not demonstrated toxic side effects upon exposure to cell lines.

In order to explore the potential toxicological effects of NAALADase inhibition, a group of mice were injected with a single peritoneal dose of 2-(phosphonomethyl) pentanedioic acid, a NAALADase inhibitor having a high activity. The dosages were given in increasing concentrations of milligrams (mg) per kilogram (kg) of body weight. Dosages of 1, 5, 10, 30, 100, 300, and 500 mg/kg (of body weight) were administered and no acute adverse effects were observed at any dose tested. The mice were subsequently observed two times per day for 5 consecutive days. Table III gives the percent survival rate for the doses tested.

TABLE III

| | NAALADase Inhibitor DOSES OF COMPOUND | | | | | | |
|---|---|---|---|---|---|---|---|
| mg/kg | 1 | 5 | 10 | 30 | 100 | 300 | 500 |
| % of animal survival as of Day 5 | 100 | 100 | 100 | 100 | 100 | 100 | 66.7 |

PHARMACEUTICALLY ACCEPTABLE DERIVATIVES

The compounds of the present invention can be used in the form of salts derived from inorganic or organic acids and bases. Included among but not limited to such acid salts are the following: acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemissulfate heptanoate, hexanoate, hydrochloride, hydrobromide, hydroiodide, 2-hydroxyethanesulfonate, lactate, maleate, methanesulfonate, 2-naphthalensulfonate, nicotinate, oxalate, pamoate, pectinate, propionate, succinate, tartrate, thiocyanate, tosylate and undecanoate. Included among but not limited to such base salts are the following: ammonium salts, alkali metal salts such as sodium and potassium salts, alkaline earth metal salts such as calcium and magnesium salts, salt with organic bases such as dicyclohexylamine salts, N-methyl-D-glucamine, and salts with amino acids such as arginine, lysine, and so forth. Also, the basic nitrogen-containing groups can be quarternized with such agents as lower alkyl halides, such as methyl, ethyl, propyl, and butyl chloride, bromides and iodides; dialkyl sulfates like dimethyl, diethyl, dibutyl and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

ROUTE OF ADMINISTRATION

For these purposes, the compounds of the present invention may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term parenteral as used herein includes subcutaneous, intravenous, intramuscular, intraperitoneally, intrathecally, intraventricularly, intrasternal and intracranial injection or infusion techniques. Generally, at the present time, invasive techniques are preferred, particularly administration directly to damaged neuronal tissue.

In addition, administration may be by a single dose, it may be repeated at intervals or it may be by continuous infusion. Where continuous infusion is preferred, pump means often will be particularly preferred for administration. Especially, subcutaneous pump means may be preferred in this regards.

Since NAALADase inhibitors are small, easily diffusible, and relatively stable, it is well suited to long-term continuous administration, such as by a perfusion pump. Also, it may be desirable to administer NAALADase inhibitors and other agents of the present invention by intraventricular injection to the affected CNS tissue on a regular basis.

Compositions and methods of the invention also may utilize controlled release technology. Thus, for example, NAALADase inhibitors may be incorporated into a hydrophobic polymer matrix for controlled release over a period of days. Such controlled release films are well known to the art. Examples of polymers commonly employed for this purpose that may be used in the present invention include nondegradable ethylene-vinyl acetate copolymer degradable lactic acid-glycolic acid copolymers, and liposomal polymers. Certain hydrogels such as poly (hydroxyethylmethacrylate) or poly(vinylalcohol) also may be useful, but for shorter release cycles then the other polymer releases systems, such as those mentioned above.

To be effective therapeutically and avoid unwanted neurological effects which may or may not be caused by NAALADase inhibitors in neural tissue, the composition should be formulated such that it will not readily penetrate the blood-brain barrier in significant amounts when peripherally administered. However, for compositions which are administered locally, such by intraperitoneal injection or by polymeric implant, such neurological concerns may be obviated.

The pharmaceutical compositions may be in the form of a sterile injectable preparation, for example as a sterile injectable aqueous or oleaginous suspension. This suspension may be formulated according to techniques know in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. Fatty acids such as oleic acid and its glyceride derivatives find use in the preparation of injectables, olive oil or castor oil, especially in their polyoxyethylated versions. These oil solutions or suspensions may also contain a long-chain alcohol diluent or dispersant.

The compounds may be administered orally in the form of capsules or tablets, for example, or as an aqueous suspension or solution. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening and/or flavoring and/or coloring agents may be added.

The compounds of this invention may also be administered in the form of suppositories for rectal administration of the drug. These compositions can be prepared by mixing the drug with a suitable non-irritating excipient which is solid at room temperature but liquid at rectal temperature and therefore will melt in the rectum to release the drug. Such materials include cocoa butter, beeswax and polyethylene glycols.

The compounds of this invention may also be administered optically, especially when the conditions addressed for treatment involve areas or organs readily accessible by topical application, including neurological disorders of the eye, the skin, or the lower intestinal tract. Suitable topical formulations are readily prepared for each of these areas. For ophthalmic use, the compounds can be formulated as micronized suspensions in isotonic, pH adjusted sterile saline, or, preferably, as solutions is isotonic, pH adjusted sterile saline, either with or without a preservative such as benzylalkonium chloride. Alternatively for the ophthalmic uses the compounds may be formulated in an ointment such as petrolatum.

For application topically to the skin, the compounds can be formulated in a suitable ointment containing the compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, the compounds can be formulated in a suitable lotion or cream containing the active compound suspended or dissolved in, for example, a mixture of one or more of the following: mineral oil, sorbitan monostearate, polysorbate 60, cetyl esters wax, cetearyl alcohol, 2-octyldodecanol, benzyl alcohol and water.

Topical application for the lower intestinal tract may be effected in a rectal suppository formulation (see above) or in a suitable enema formulation.

DOSE

Dosage levels on the order of about 0.1 mg to about 10,000 mg of the active ingredient compound are useful in the treatment of the above conditions, with preferred levels of about 0.1 mg to about 1,000 mg. The amount of active ingredient that may be combined with the carrier materials to produce a single dosage form will vary depending upon the host treated and the particular mode of administration.

It is understood, however, that a specific dose level for any particular patient will depend upon a variety of factors including the activity of the specific compound employed, the age, body weight, general health, sex, diet, time of administration, rate of excretion, drug combination, and the severity of the particular disease being treated and form of administration.

Treatment dosages generally may be titrated to optimize safety and efficacy. Typically, dosage-effect relationships from in vitro initially can provide useful guidance on the proper doses for patient administration. Studies in animal models also generally may be used for guidance regarding effective dosages for treatment of cancers in accordance with the present invention. In terms of treatment protocols, it should be appreciated that the dosage to be administered will depend on several factors, including the particular analog that is administered, the route administered, the condition of the particular patient, etc. In that most of these agents have peptidyl portions it will generally be desirable to administer the agents I.V., but administration by other routes is contemplated where appropriate. Generally speaking, one will desire to administer an amount of the agent that is effective to achieve a serum level commensurate with the concentrations found to be effective in vitro. Thus, where an agent is found to demonstrate in vitro activity at, e.g., 10 $\mu$M, one will desire to administer an amount of the drug that is effective to provide about a 10 $\mu$M concentration in viva. Determination of these parameters are well within the skill of the art.

These considerations, as well as effective formulations and administration procedures are well known in the art and are described in standard textbooks.

A particular formulation of the invention uses a lyophilized form of NAALADase inhibitor, in accordance with well known techniques. For instance, 1 to 100 mg of NAALADase inhibitor may be lyophilized in individual vials, together with carrier and buffer compound, for instance, such as mannitol and sodium phosphate. The NAALADase inhibitor may be reconstituted in the vials with bacteriostatic water and then administered, as described elsewhere herein.

Compositions of the present invention for treating global ischemia are administered internally to a subject and contain an effective amount of a NAALADase inhibitor. Doses included in the pharmaceutical compositions are of an efficacious, nontoxic quantity. Persons skilled in the art using routine clinical testing are able to determine optimum doses. The desired dose is administered to a subject from 1 to 6 or more times daily, orally, rectally, parenterally, or topically and may follow a higher initial amount administered as a bolus dose.

ADMINISTRATION REGIMEN

Any effective treatment regimen can be utilized and readily determined and repeated as necessary to effect treatment.

In clinical practice, the compositions containing NAALADase inhibitor alone or in combination with other therapeutic agents are administered in specific cycles until a response is obtained.

a. Administration for Nervous Insult

The present invention is directed to regimens which dictate the timing and sequence of delivery of treatment medications to include pretreatment. To maximize protection of nervous tissue from nervous insult, the compounds of the present invention should be administered is as soon as possible within the affected cells. This would include administration before the nervous ischemic insult in situations of increased likelihood of ischemia or stroke. Known in anticipatory situations of include surgery (cartoid endarterectomy, cardiac, vascular, aortic, orthopedic), endovascular procedures such as any type of arterial catherization (cartoid, vertebral, aortic, cardia, renal, spinal, Adamkiewicz and others) for diagnostic or therapeutic purposes including evaluation and treatment of vascular stenosis, aneurysm or arteriovenous malformation and or injection of embolic agents, coils or balloons for hemostasis, interruption of vascularity or treatment of brain lesions, predisposing medical conditions, including crescendo transient ischemic attacks, anticipated emboli or sequential strokes. Where pretreatment for stroke or ischemia is not possible or practicable, it is important to get the compounds of the present invention to the affected cells as quickly as possible during or after the event. The time between the stroke, diagnosis and treatment should be reduced to its minimum to save the ischemic cells from damage and death.

b. Administration for Prostate Disease/Cancer

For patients who initially present without advanced or metastatic cancer, NAALADase inhibitor based drugs are used as an immediate initial therapy prior to surgery and radiation therapy, and as a continuous post-treatment therapy in patients at risk for recurrence or metastasis (based upon high PSA, high Gleason's score, locally extensive disease, and/or pathological evidence of tumor invasion in the surgical specimen). The goal in these patients is to inhibit the growth of potentially metastatic cells from the primary tumor during surgery or radiotherapy and inhibit the growth of tumor cells from undetectable residual primary tumor.

For patients who initially present with advanced or metastatic cancer, NAALADase inhibitor based drugs are used as a continuous supplement to, or possible as a replacement for hormonal ablation. The goal in these patients is to slow tumor cell growth from both the untreated primary tumor and from the existing metastatic lesions.

In addition, the invention may be particularly efficacious during post-surgical recovery, where the present compositions and methods may be particularly effective in lessening the chances of recurrence of a tumor engendered by shed cells that cannot be removed by surgical intervention.

COMBINATION WITH OTHER TREATMENTS a. Nervous Insult

In compositions for treating stroke, particularly acute ischemic stroke, and global ischemia caused by drowning, head trauma and so forth, the NAALADase inhibitor can be co-administered with one or more agents active in reducing the risk of stroke, such as aspirin or ticlopidine (preferably ticlopidine, which has been demonstrated to reduce the risk of a second ischemic event). Co-administration can be in the form of a single formulation (combining, for example, a NAALADase inhibitor and ticlopidine with pharmaceutically acceptable excipients, optionally segregating the two active ingredients in different excipient mixtures designed to independently control their respective release rates and durations) or by independent administration of separate formulations containing the active agents.

If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

The compounds of this invention are generally administered in a pharmaceutical composition which comprises a pharmaceutical excipient or excipients in combination with a NAALADase inhibitor. The level of the drug in a formulation can vary within the full range employed by those skilled in the art, namely, from about 0.01 percent weight (% w) to about 99.99% w of the drug based on the total formulation and about 0.01% w to 99.99% w excipient. Preferably, the formulation will be about 3.5 to 60% by weight of the NAALADase inhibitor, with the rest being suitable pharmaceutically excipients.

b. Prostate Disease/Cancer

Surgery and Radiation

In general, surgery and radiation therapy are employed as potentially curative therapies for patients under 70 years of age who present with clinically localized disease and are expected to live at least 10 years.

Approximately 70% of newly diagnosed prostate cancer patients fall into this category. Approximately 90% of these patients (65% of total patients) undergo surgery, while approximately 10% of these patients (7% of total patients) undergo radiation therapy.

Histopathological examination of surgical specimens reveals that approximately 63% of patients undergoing surgery (40% of total patients) have locally extensive tumors or regional (lymph node)metastasis that was undetected at initial diagnosis. These patients are at a significantly greater risk of recurrence. Approximately 40% of these patients will actually develop recurrence within five years after surgery. Results after radiation are even less encouraging. Approximately 80% of patients who have undergone radiation as their primary therapy have disease persistence or develop recurrence or metastasis within five years after treatment.

Currently, most of these surgical and radiotherapy patients generally do not receive any immediate follow-up therapy. Rather, they are monitored frequently for elevated Prostate Specific Antigen ("PSA"), which is the primary indicator of recurrence or metastasis.

Thus, there is considerable opportunity to use the present invention in conjunction with surgical intervention.

Hormonal Therapy

Hormonal ablation is the most effective palliative treatment for the 10% of patients presenting with metastatic prostate cancer at initial diagnosis. Hormonal ablation by medication and/or orchiectomy is used to block hormones that support the further growth and metastasis of prostate cancer. With time, both the primary and metastatic tumors of virtually all of these patients become hormone-independent and resistant to therapy. Approximately 50% of patients presenting with metastatic disease die within three years after initial diagnosis, and 75% of such patients die within five years after diagnosis. Continuous supplementation with NAALADase inhibitor based drugs are used to prevent or reverse this potentially metastasis-permissive state.

Chemotherapy

Chemotherapy has been more successful with some cancers than with others. It is likely that the combination of chemotherapy with therapies of the present invention in some cases will be synergistic. However, chemotherapy currently has little effect on prostate cancer and is generally reserved as a last resort, with dismal results. For this type of cancer, the opportunity to combine chemotherapy with methods and compositions of the invention will be rare.

Immunotherapy

The NAALADase inhibitors may also be used in combination with monoclonal antibodies in treating prostate cancer. Because pelvic lymph node involvement affects the 5-year survival rate—84% of patients without pelvic lymph node involvement survive 5 years, compared with only 34% of those having pelvic lymph node involvement, the use of NAALADase inhibitors in combination with monoclonal antibodies becomes significant. A specific example of such an antibody includes cell membrane-specific anti-prostate antibody.

The present invention may also be used with immunotherapies based on polyclonal or monoclonal antibody-derived reagents, for instance. Monoclonal antibody-based reagents are most preferred in this regard. Such reagents are well known to persons of ordinary skill in the art. Radiolabelled monoclonal antibodies for cancer therapy, such as the recently approved use of monoclonal antibody conjugated with strontium-89, also are well known to persons of ordinary skill in the art.

Cryotherapy

Cryotherapy recently has been applied to the treatment of some cancers. Methods and compositions of the present invention also could be used in conjunction with an effective therapy of this type.

Combinations with other Active Agents

According to another aspect of the invention, pharmaceutical compositions of matter useful for inhibiting cancer are provided that contain, in addition to the aforementioned compounds, an additional therapeutic agent. Such agents may be chemotherapeutic agents, ablation or other therapeutic hormones, antineoplastic agents, monoclonal antibodies useful against cancers and angiogenesis inhibitors. The following discussion highlights some agents in this respect, which are illustrative, not limitative. A wide variety of other effective agents also may be used.

Among hormones which may be used in combination with the present inventive compounds, diethylstilbestrol (DES), leuprolide, flutamide, cyproterone acetate, ketoconazole and amino glutethimide are preferred.

Among antineoplastic and anticancer agents that may be used in combination with the inventive compounds, 5-fluorouracil, vinblastine sulfate, estramustine phosphate, suramin and strontium-89 are preferred. Other chemotherapeutics useful in combination and within the scope of the present invention are buserelin, chlorotranisene, chromic phosphate, cisplatin, cyclophosphamide, dexamethasone, doxorubicin, estradiol, estradiol valerate, estrogens conjugated and esterified, estrone, ethinyl estradiol, floxuridine, goserelin, hydroxyurea, melphalan, methotrexate, mitomycin and prednisone.

Table IV provides known median dosages for selected cancer agents which may be useful in combination with the compounds and compositions of the present invention. It should be noted that specific dose levels for the chemotherapeutic agents below will depend upon similar dosing considerations as those listed in the DOSAGE section for NAALADase inhibitors presented herein.

TABLE IV

| NAME OF CHEMOTHERAPEUTIC AGENT | MEDIAN DOSAGE |
| --- | --- |
| Asparaginase | 10,000 units |
| Bleomycin Sulfate | 15 units |
| Carboplatin | 50–450 mg. |
| Carmustine | 100 mg. |
| Cisplatin | 10–50 mg. |
| Cladribine | 10 mg. |
| Cyclophosphamide (lyophilized) | 100 mg.–2 gm. |
| Cyclophosphamide (non-lyophilized) | 100 mg.–2 gm. |
| Cytarabine (lyophilized powder) | 100 mg.–2 gm. |
| Dacarbazine | 100 mg.–200 mg. |
| Dactinomycin | 0.5 mg. |
| Daunorubicin | 20 mg. |
| Diethylstilbestrol | 250 mg. |
| Doxorubicin | 10–150 mg. |
| Etidronate | 300 mg. |
| Etoposide | 100 mg. |
| Floxuridine | 500 mg. |
| Fludarabine Phosphate | 50 mg. |
| Fluorouracil | 500 mg.–5 gm. |
| Goserelin | 3.6 mg. |
| Granisetron Hydrochloride | 1 mg. |
| Idarubicin | 5–10 mg. |
| Ifosfamide | 1–3 gm. |
| Leucovorin Calcium | 50–350 mg. |
| Leuprolide | 3.75–7.5 mg. |
| Mechlorethamine | 10 mg. |
| Medroxyprogesterone | 1 gm. |
| Melphalan | 50 gm. |
| Methotrexate | 20 mg.–1 gm. |
| Mitomycin | 5–40 mg. |
| Mitoxantrone | 20–30 mg. |
| Ondansetron Hydrochloride | 40 mg. |
| Paclitaxel | 30 mg. |
| Pamidronate Disodium | 30–*90 mg. |
| Pegaspargase | 750 units |
| Plicamycin | 2,500 mcgm. |
| Streptozocin | 1 gm. |
| Thiotepa | 15 mg. |
| Teniposide | 50 mg. |
| Vinblastine | 10 mg. |
| Vincristine | 1–5 mg. |
| Aldesleukin | 22 million units |
| Epoetin Alfa | 2,000–10,000 units |
| Filgrastim | 300–480 mcgm. |
| Immune Globulin | 500 mg.–10 gm. |
| Interferon Alpha-2a | 3–36 million units |
| Interferon Alpha-2b | 3–50 million units |
| Levamisole | 50 mg. |
| Octreotide | 1,000–5,000 mcgm. |
| Sargramostim | 250–500 mcgm. |

In Vitro Assay of NAALDase Inhibitors on Ischemia

Referring now to FIG. 1 of the drawings, the effect of different doses of 2-(Phosphonomethyl)pentanedioic Acid on the amount of in vitro toxicity following ischemic insult in cortical cultures is shown. Concentrations ranging from 100 pM to 1 $\mu$M of 2-(Phosphonomethyl)pentanedioic Acid administered during ischemic insult and for one hour following show a sharp decrease in the amount of in vitro toxicity. The percentages concerning the toxicity for different doses is shown graphically in FIG. 1. The numerical percentages are also provided below in Table IV.

TABLE IV

| Dose | % Toxicity |
| --- | --- |
| Control | 100. ± 9.0   (n = 5) |
| 100 pM | 66.57 ± 4.38 (n = 5) |
| 1 nM | 42.31 ± 9.34 (n = 5) |
| 10 nM | 33.08 ± 9.62 (n = 5) |
| 100 nM | 30.23 ± 9.43 (n = 5) |
| 1 uM | 8.56 ± 8.22 (n = 5) |

The methods for obtaining the data shown above in Table IV and graphically represented in FIG. 1 are set forth in the protocol described in Example 11, below.

Ischemia was then induced using potassium cyanide and 2-deoxyglucose (2-DG) in a standard technique, such as that described below.

Cultures and media were then assayed according to standard cytologic cell injury assay, such as the LDH Assay set forth and described below.

In Vitro Toxicity of NAAG on Cortical Cultures

Figure 2:
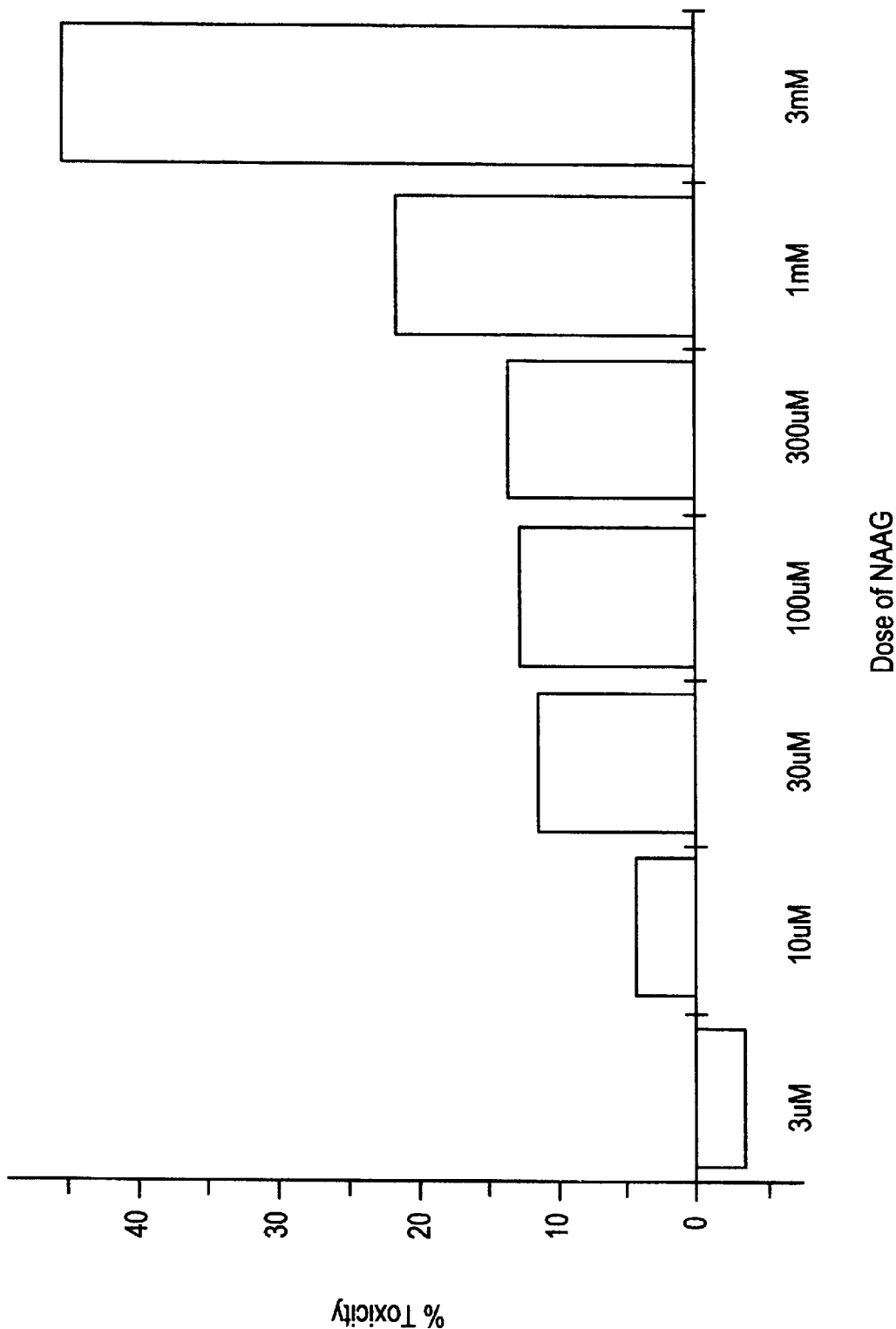
FIG. 2 is a bar graph plotting in vitro toxicity of various doses of NAAG in cortical cultures.

Referring now to FIG. 2 of the drawings, NAAG toxicity in cortical cell cultures is plotted graphically against various dosages of NAAG. Dosages of NAAG are administered for 20 minutes and range from 3 uM to 3 mM, and include 3 uM, 10 uM, 30 uM, 100 uM, 300 uM, 1 mM, and 3 mM. Numerical results of the percentage toxicity are also shown in Table V, below.

TABLE V

| Dose of NAAG | % Toxicity |
| --- | --- |
| 3 $\mu$M | 3.51 (n = 1) |
| 10 $\mu$M | 4.3 ± 3.12 (n = 3) |
| 30 $\mu$M | 11.40 ± 6.17 (n = 3) |
| 100 $\mu$M | 12.66 ± 5.50 (n = 3) |
| 300 $\mu$M | 13.50 ± 4.0 (n = 3) |
| 1 mM | 21.46 ± 4.20 (n = 3) |
| 3 mM | 45.11 ± 4.96 (n = 3) |

In Vitro Assay of NAAG toxicity as blocked by Example 3

Figure 3:
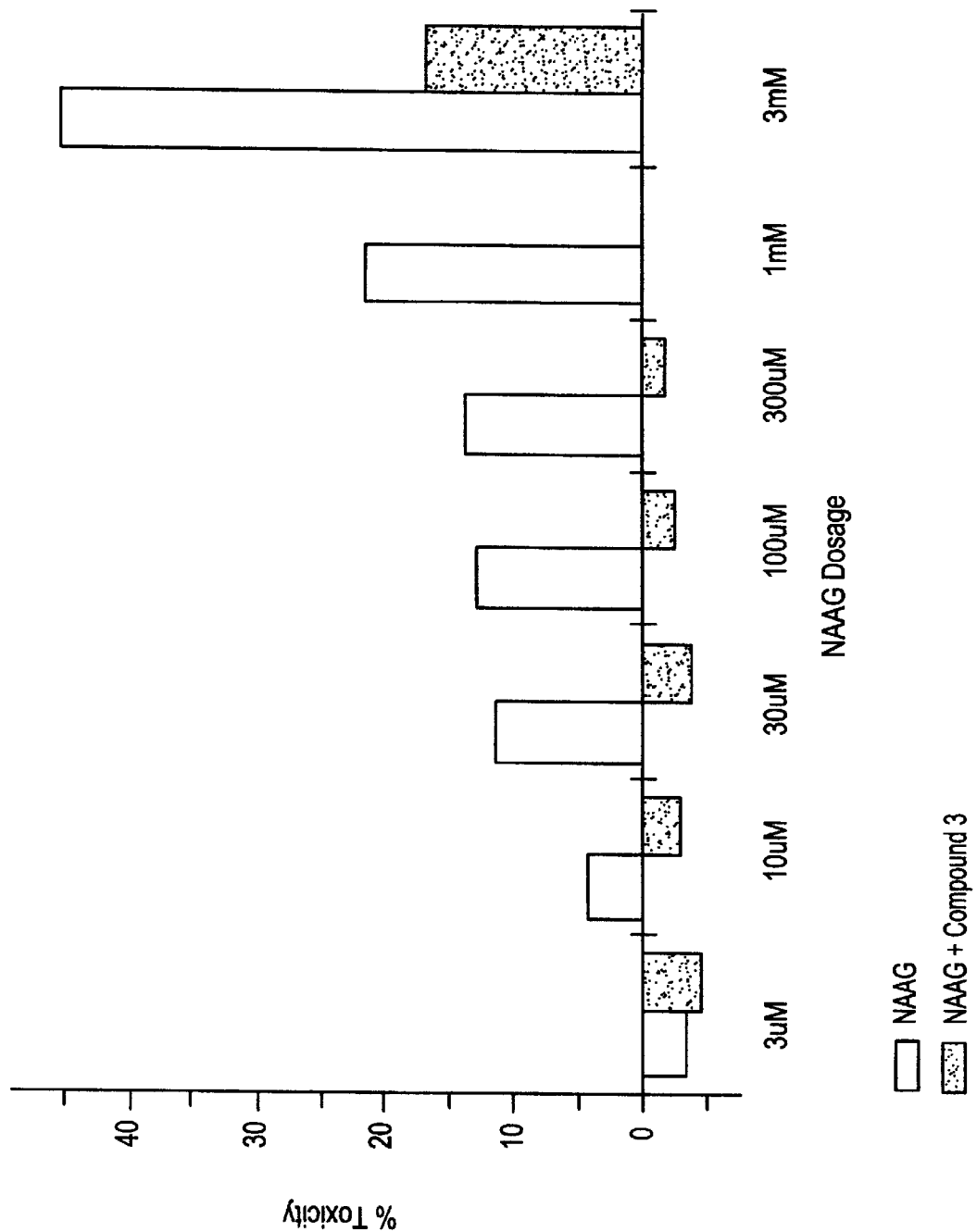
FIG. 3 is a bar graph plotting in vitro NAAG toxicity in cortical cultures blocked by various dosages of 2-(Phosphonomethyl)pentanedioic Acid.

Referring now to FIG. 3 of the drawings, NAAG toxicity in cortical cell cultures is graphically plotted against NAAG toxicity in the presence of 2-(Phosphonomethyl) pentanedioic Acid (1 $\mu$M). 2-(Phosphonomethyl) pentanedioic Acid is administered during exposure to NAAG and for one hour following NAAG exposure. Numerical results of the comparative toxicity are also shown in the percentages of Table VI. Clearly, comparing the results of FIG. 2/Table V and FIG. 3/Table VI show the remarkable protective effects of the compounds of the present against nervous insult or neuronal damage.

TABLE VI

| Dose of NAAG | % Toxicity with Example 3 |
| --- | --- |
| 3 $\mu$M | -4.71 (n = 1) |
| 10 $\mu$M | -3.08 ± 0.81 (n = 3) |
| 30 $\mu$M | -4.81 ± 1.13 (n = 3) |
| 100 $\mu$M | -2.87 ± 0.78 (n = 3) |
| 300 $\mu$M | -2.09 ± 0.48 (n = 3) |

TABLE VI-continued

| Dose of NAAG | % Toxicity with Example 3 |
|---|---|
| 1 mM | 0.26 ± 1.11 (n = 3) |
| 3 mM | 16.83 ± 8.76 (n = 3) |

Since NAAG is cleaved by NAALADase to release glutamate, adding NAAG to cortical cultures in the absence of NAALADase inhibitors is shown to be toxic in FIG. 2 (control). FIGS. 2 and 3 show that the addition of NAALADase inhibitors along with NAAG provides protection against glutamate-induced neurotoxicity in vitro.

Figure 4:
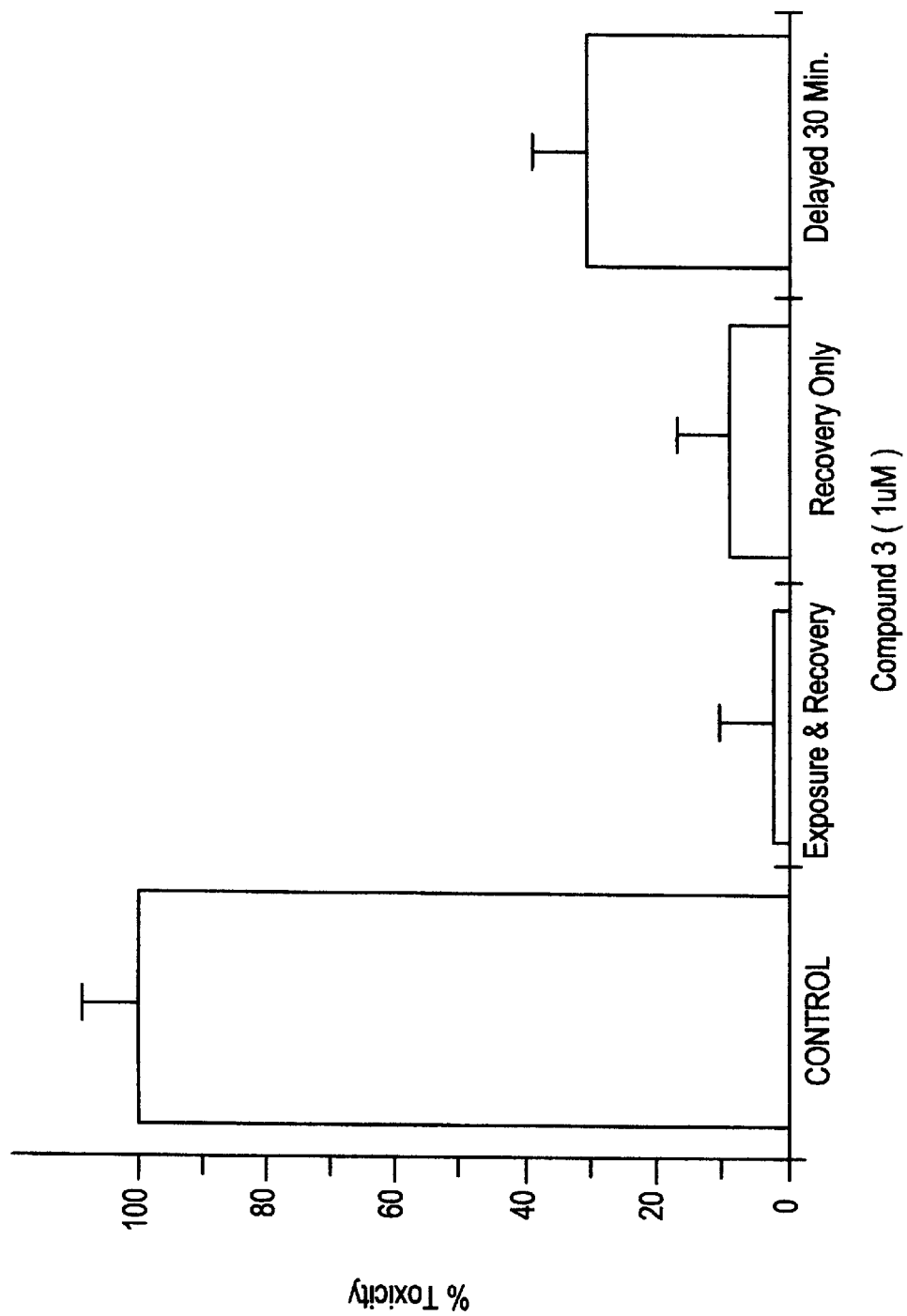
FIG. 4 is a bar graph plotting in vitro toxicity of an ischemic event in cortical cultures in the presence of 2-(Phosphonomethyl)pentanedioic Acid administered at different times of exposure to the ischemic event.

NAALADASE Inhibitors are Protective When Administered Post-Ischemia in Cortical Cultures Referring now to FIG. 4 of the drawings, ischemic toxicity in cortical cultures is graphically plotted against the time of administration of 2-(Phosphonomethyl)pentanedioic Acid. 2-(Phosphonomethyl)pentanedioic Acid is administered during the exposure to the ischemic insult and for one hour following (exposure and recovery), for one hour post ischemic insult only (recovery only), and for one hour beginning 30 minutes post ischemic insult (delayed 30 minutes). Remarkable in vitro protective effects are shown not only when the compounds of the present invention are administered during exposure to the ischemic event and during recovery from the ischemic event, but also that significant neuronal protection may be achieved when administration of the compositions of the present invention are delayed 30 minutes. Numerical results of the percentage toxicity are also shown in Table VII.

TABLE VII

| Time of Administration relative to Ischemic Event | % Toxicity |
|---|---|
| CONTROL | 100% |
| Exposure & Recovery | 2.54% |
| Recovery Only | 9.03% |
| Delayed 30 minutes | 31.49% |

In Vivo Infarct Volume After Administration

Because the in vitro results using 2-(Phosphonomethyl)pentanedioic Acid were so strikingly protective against injury from ischemic insult, the in vivo neuroprotection using 2-(Phosphonomethyl)pentanedioic Acid is also examined.

Figure 5:
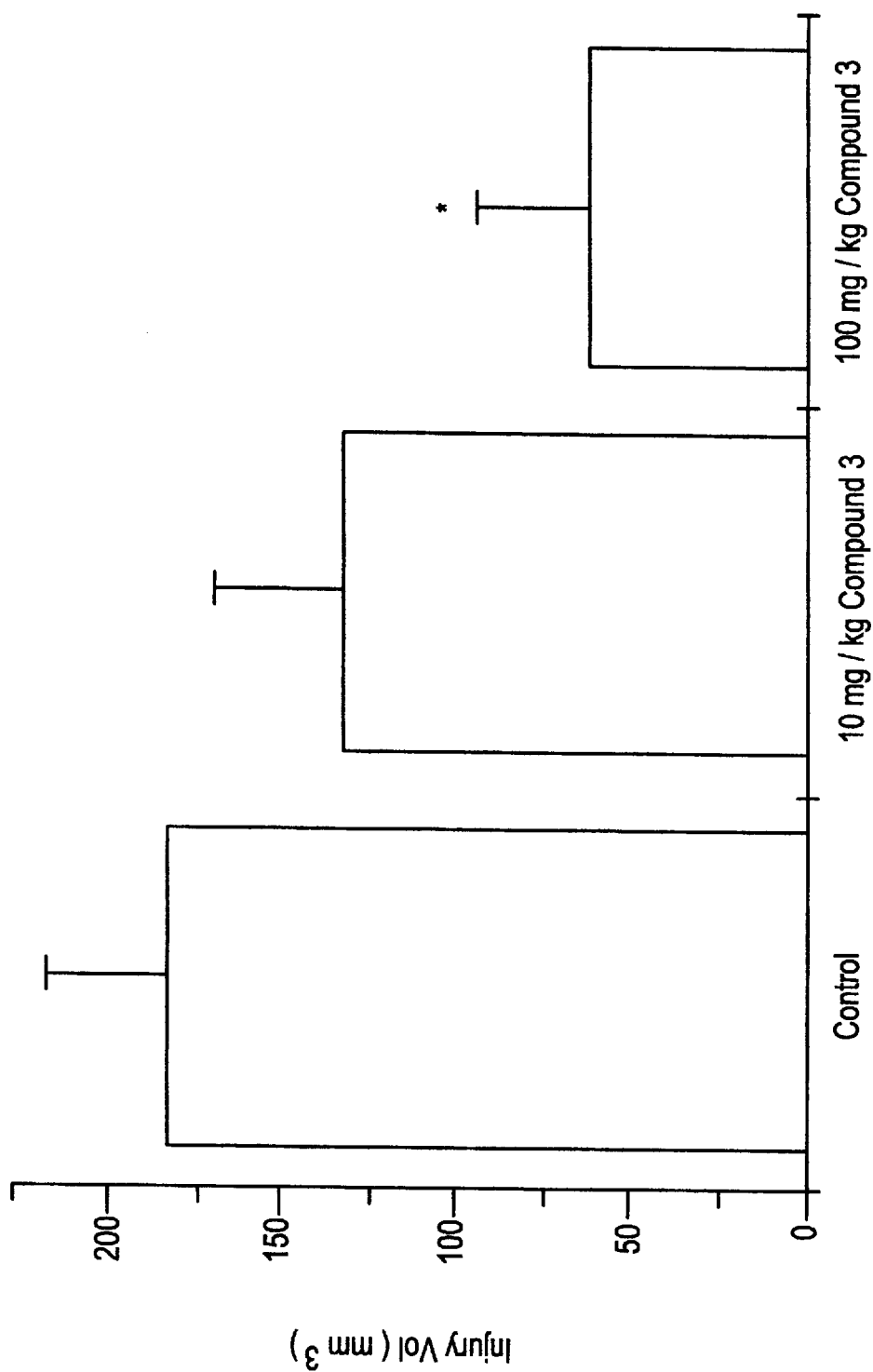
FIG. 5 is a bar graph plotting the in vivo cortical injury volume in rats following middle cerebral artery occlusion in which various dosages of 2-(Phosphonomethyl) pentanedioic Acid were administered during the ischemia and for one hour during reperfusion.

Referring now to FIG. 5 and to Table VIII below, infarct volume measuring injury to the cortex is evaluated in rats following middle cerebral artery occlusion (see Example 12). Control animals receive saline, other animals receive 10 mg/kg of 2-(Phosphonomethyl)pentanedioic Acid followed by 2 mg/kg/hr of 2-(Phosphonomethyl)pentanedioic Acid for 1 hour, and still others receive 100 mg/kg of 2-(Phosphonomethyl)pentanedioic Acid followed by 20 mg/kg/hr of 2-(Phosphonomethyl)pentanedioic Acid for one hour. Again, in vivo protective effects, as demonstrated by the significantly reduced injury volume are shown when the compounds of the present invention are administered during exposure to the ischemic event. Results of the infarct volume testing, shown graphically in FIG. 5 and numerically below in Table VIII, show that in high dose administration of compounds of the present invention significant protection of the cortex may be achieved in vivo.

TABLE VIII

| Cortical Injury Volume (mm3) ± S.E.M. | |
|---|---|
| Vehicle | 184.62 ± 33.52 (n = 10) |
| 10 mg/kg Example 3 | 135 ± 32.18 (n = 10) |
| 100 mg/kg Example 3 | 65.23 ± 32.18 (n = 10) |
| Cortical Injury Volume (% injury) ± S.E.M. | |
| vehicle | 34.44 ± 6.53 (n = 10) |
| 10 mg/kg Example 3 | 29.14 ± 7.68 (n = 10) |
| 100 mg/kg Example 3 | 13.98 ± 6.64 (n = 10) |
| Cortical Protection | |
| Vehicle | 0% |
| 10 mg/kg Example 3: | 27% |
| 100 mg/kg Example 3 | 65% |

In Vitro Neurotoxicity Assay a. Cell Culture

Dissociated cortical cultures are prepared using the papain-dissociation method of Heuttner and Baughman (1986) as modified by Murphy and Baraban (1990). See Table IX for the Dissociated Culture Protocol as used herein. Fetuses of embryonic day 17 are removed from timed pregnancy rats (Harlan Sprague Dawley). The cortex is rapidly dissected out in Dulbecco's phosphate-buffered saline, stripped of meninges, and incubated in a papain solution for 15 min at 37° C. The tissue is then mechanically triturated and pelleted at 500 g (1000–2000 rpm on swinging bucket Beckman). The pellet is resuspended in a DNAase solution, triturated with a 10 mL pipette x15-20, layered over a "10×10" solution containing albumin and trypsin inhibitor (see Table IX for an example of a "10×10" solution), repelleted, and resuspended in a plating medium containing 10% fetal bovine serum (HyClone A-1111-L), 5% heat-inactivated Equine serum (HyClone A-3311-L), and 84% modified Earle's basal medium (MEM)(Gibco 51200-020) with high glucose (4.5 g/L), and 1 g/L $NaHCO_3$. Each 24-well plate is pretreated with poly-D-lysine (0.5 ml/well of 10 μg/ml) for 1 h and rinsed with water before plating. Cultures are plated at 2.5×10⁶ cells/ml with each well of a 24 well plate receiving 500 μl/well. Alternatively, 35 mm dishes can be plated at 2 mls/dish, 6 well plates at 2 mls/well, or 12 well plates at 1 ml/well. After plating, 50% of the medium is changed every 3–4 days with growth serum containing 5% heat-inactivated Equine serum (HyClone A-3311-L), 95% modified Earle's basal medium (MEM) (Gibco 51200-020), and 1% L-Glutamine (Gibco 25030-081). Experiments are performed after 21 days in cultures. Cultures are maintained in a 5% $CO_2$ atmosphere at 37° C. A detailed description of these methodologies is further described in the table below.

TABLE IX

| DISSOCIATED CULTURE PROTOCOL | |
|---|---|
| I. PREPARE SOLUTIONS | |
| Stocks/Solutions: | |
| DNAase Stock, 1 mL (100×) 5 mgs of DNAase I (Worthington LS002004); 1 ml dissoc. EBSS | Dulbecco's PBS, 500 mL 4 gms NaCl (J. T. Baker 3624-01); 1.06 gms $Na_2HPO_4 \cdot 7H_2$) (Fisher S373-3); |

TABLE IX-continued

DISSOCIATED CULTURE PROTOCOL

| | |
|---|---|
| Freeze as 50 ul aliquots. | 100 mg KCl (Fisher P217-500); 100 mg KH$_2$PO$_4$ (Sigma P-0662); 500 mls dH$_2$O; Adjust pH to 7.4 and sterile filter. |
| Dissociated EBSS, 500 mL 1.1 gms NaHCO$_3$; 50 mls EBSS stock (Gibco 14050-025); 450 mls dH$_2$O; Sterile filter. | EDTA Stock, 10 mL 184.2 mgs EDTA sodium salt (Sigma ED4S); 10 mls dH$_2$O; Sterile filter. |
| 10 and 10 Stock, 10 mL 100 mg BSA (Sigma A-4919); 100 mg Trypsin Inhibitor from Egg White (Sigma T-2011); 10 mls dissoc. EBSS; Sterile filter. Media | Poly-D-Lysine Stock, 5 mL 5 mg Poly-D-Lysine, 100–150K (Sigma P-6407); 5 mls sterile water; Keep frozen. |
| Dissociated growth, 500 mL 500 mls MEM (Gibco 51200-020) containing glucose and NaHCO$_3$ (2.25 gm glucose and 0.5 gm NaHCO$_3$); 25 mls heat-inactivated Equine Serum (HyClone A-3311-L); 5 mls L-Glutamine (200 mM, 100x stock, Gibco 25030-081); Sterile filter. | Plating media, 300 mL 250 mls MEM containing glucose and sodium bicarbonate (2.25 gm glucose and 0.5 gm NaHCO$_3$ in 500 mls Gibco MEM 51200-020); 30 MLS Fetal Bovine Serum (HyClone A-1111-L); 15 mls heat-inactivated Equine Serum (HyClone A-3311-L); 3 mls L-Glutamine (200 mM, 100x stock, Gibco 25030-081); 1 ml Penicillin-Streptomycin stock (Gibco 15140-015); Sterile filter. |
| For papain dissociation: 4 mg Cysteine (C-8277); 25 mls dissoc. EBSS; 250 μl Papain stock (Worthington LS003126); Place in 37° C. waterbath until clear. | For DNAase treatment: DNAase, 5 mL 4.5 mls dissoc. EBSS; 500 μl "10 and 10" stock; 50 μl DNAase stock. '10 and 10', 5 mL 4.5 mls of EBSS; 500 μl '10 and 10' stock |

II. COAT DISHES

Use poly-d-lysine stock at 1:100 dilution to coat 24-well plates (0.5 ml/well) or at 1:10 dilution to coat 35 mm glass cover slips (1.0 ml/coverslip).
Leave until end of dissection.

III. DISSECT TISSUE

Use Harlan Sprague-Dawley timed pregnancy rats, ordered to arrive at E-17.
Decapitate, spray abdomen down with 70% EtOH.
Remove uterus through midline incision and place in sterile dPBS.
Remove brains from embryos, leaving them in dPBS.
Brain removal: Penetrate skull and skin with fine forceps at lambda. Pull back to open posterior fossa. Then move forceps anteriorly to separate sagittal suture. Brain can be removed by scooping back from olfactory bulbs under the brain.
Move brains to fresh dPBS; subsequently, dissect away from cortex.

IV. PAPAIN DISSOCIATION

Transfer cortices equally to two 15 ml tubes containing sterile papain solution, maintained at 37° C.
Triturate x1 with sterile 10 ml pipette.
Incubate only for 15 minutes at 37° C.
Spin at 500 G for 5 minutes (1000–2000 RPM on swinging bucket Beckman).

V. DNAase TREATMENT

Remove supernatant and any DNA gel layer from cell pellet (or pick up and remove pellet with pipette).
Move cell pellet to DNAase solution.
Triturate with 10 ml pipette, x15–20.
Layer cell suspension over the '10 and 10' solution by pipetting it against the side of the tubes.
Spin again at 500 G for 5 minutes. (Cells with spin into "10 and 10" LAYER).
Wash tube sides with plating media without disturbing pellett.
Pipette off the media wash and repeat the wash.

VI. PLATE

Add about 4.5 mls plating media to each pellet for 5 ml volume.
Re-suspend with 10 ml pipette.
Pool cells into a single tube.
Quickly add 10 μl of the suspended cells to a hemocytometer so that they don't settle.
Count cells per large square, corresponding to 10 million cells/ml.
Put re-suspended cells into a larger container so that they number 2.5 million cells/ml (Thus if there Triturate to homogeneity).
Finish coating plates:
Aspirate or dump Lysine;
Wash x1 with sterile water and dump.
Add plating media, with cells, to the plates as follows:

| | |
|---|---|
| 35 mm dishes | 2 mls/dish; |
| 6 well plate | 2 mls/well; |
| 12 well plate | 1 ml/well; |
| 24 well plate | 500 μl/well. |

VII. FEED

Cultures are usually made on Thursdays
Start feeding twice a week; beginning the following Monday, feeding Mondays and Fridays.
Remove 50% of volume and replace with fresh growth media.

b. Ischemic Insult using potassium cyanide and 2-deoxyglucose

Twenty-one to twenty-four days following the initial cortical cell plating, the experiment is performed. The cultures are washed three times in HEPES buffered saline solution containing no phosphate. The cultures are then exposed to potassium cyanide (KCN) (5mM) and 2-deoxyglucose (2-DG) (10 mM) for 20 minutes at 37° C. These concentrations were shown previously to induce maximal toxicity (Vornov et al., J.Neurochem, 1995, Vol. 65, No. 4, pp. 1681–1691). At the end of 24 hours, the cultures are analyzed for release of the cytosolic enzyme lactate dehydrogenase (LDH), a standard measure of cell lysis. LDH measurements are performed according to the method of Koh and Choi (J.Neuroscience Methods, 1987; see example 11).

c. NAAG Induced Neurotoxicity

Cultures are assessed microscopically and those with uniform neuronal densities are used in the NAAG neurotoxicity trials.

At the time of the experiment, the cultures are washed once in HEPES-buffered saline solution (HBSS; NaCl 143.4 mM, HEPES 5 mM, KCl 5.4 mM, MgSO$_4$ 1.2 mM, NaH$_2$PO$_4$ 1.2 mM, CaCl$_2$ 2.0 MM, D-glucose 10 mM)

(Vornov et al., 1995) and then exposed to various concentrations of NAAG for 20 minutes at 37° C. NAAG concentrations range from 3 μM to 3 mM, and include 3 μM, 10 μM, 30 μM, 100 μM, 300 μM, 1 mM, and 3 mM. At the end of exposure, the cells are washed once with HEPES buffered saline solution and then replaced with serum free modified Earle's basal medium. The cultures are then returned to the $CO_2$ incubator for 24 hour recovery.

d. Lactate Dehydrogenase Assay

Release of the cytosolic enzyme lactate dehydrogenase (LDH), a standard measure of cell lysis, is used to quantify injury (Koh and Choi, 1987). LDH-activity measurements are normalized to control for variability between culture preparations (Koh et al., 1990). Each independent experiment contains a control condition in which no NAALADase inhibitors are added; a small amount of LDH activity is found in these controls. This control measurement is subtracted from each experimental point. These values are normalized within each experiment as a percentage of the injury caused by NAAG/ischemia. Only main effects of NAALADase inhibitors are considered; interactions between dose and condition are not examined statistically.

A measurement of the potency of each compound tested is made by measuring the percentage of LDH release into the growth media after exposure to NAAG/ischemia plus NAALADase inhibitor or NAAG/ischemia plus saline (control). Since high concentrations of glutamate may be toxic to cells in certain circumstances, measurement of glutamate toxicity is observed using LDH as a standard measurement technique.

In Vivo Neurotoxicity Assay a. Materials and method

A colony of SHRSP rats is bred at Johns Hopkins School of Medicine from three pairs of male and female rats obtained from the National Institutes of Health (Laboratory, Sciences Section, Veterinary Resources Program, National Center for Research Resources, Bethesda, Md.). All rats are kept in a virus-free environment and maintained on regular diet (NIH 31, Zeigler Bros, Inc.) with water ad libitum. All groups of rats are allowed to eat and drink water until the morning of the experiment.

Transient occlusion of the middle cerebral artery (MCA) is induced by advancing a 4-0 surgical nylon suture into the internal carotid artery (ICA) to block the origin of the MCA (Koizumi, 1986; Longa, 1989; Chen, 1992). Briefly, animals are anesthetized with 4% halothane, and maintained with 1.0 to 1.5% halothane in air enriched oxygen using a face mask. Rectal temperature is maintained at 37.0°±0.5° C. throughout the surgical procedure using a heating lamp. The right femoral artery is cannulated for measuring blood gases (pH, oxygen tension [PO2], carbon dioxide tension [PCO2]) before and during ischemia, for monitoring blood pressure during the surgery. The right common carotid artery (CCA) is exposed through a midline incision; a self-retraining retractor is positioned between the digastric and mastoid muscles, and the omohyoid muscle is divided. The right external carotid artery (ECA) is dissected and ligated. The occipital artery branch of the ECA is then isolated and coagulated. Next, the right internal carotid artery (ICA) is isolated until the pterygopalatine artery is exposed, and carefully separated from the adjacent vagus nerve. The pterygopalatine artery is ligated with 4-0 silk suture close to its origin.

After the CCA is ligated with 4-0 silk suture, a 4-0 silk suture to prevent bleeding from a puncture site, through which a 2.5 cm length of 4-0 monofilament nylon suture (Ethilon), its tip rounded by heating near a electric cautery, is introduced into the ICA lumen. A 6-0 silk suture is tightened around the intraluminal nylon suture at the bifurcation to prevent bleeding, and the stretched sutures at the CCA and the ICA are released. The nylon suture is then gently advanced as far as 20 mm.

Anesthesia is terminated after 10 minutes of MCA occlusion in both groups, and animals awakened 5 minutes thereafter. After 2 hours of ischemia, anesthesia is reanesthetized, and reperfusion is performed by withdrawing the intraluminal nylon suture until the distal tip became visible at the origin of the ICA.

Arterial pH and PaCO2, and partial pressure of oxygen (PaO2) are measured with a self-calibrating Radiometer electrode system (ABL 3; Copenhagen, Denmark). Hemoglobin and arterial oxygen content are measured with a hemoximeter (Radiometer, Model OSM3; Copenhagen, Denmark). Blood glucose is measured with a glucose analyzer (model 2300A, Yellow Springs Instruments, Yellow Springs, Ohio).

Each group is exposed to 2 hours of right MCA occlusion and 22 hours of reperfusion. All variables but the rectal temperature are measured at baseline, at 15 minutes and 45 minutes of right MCA occlusion. The rectal temperature is measured at baseline, at 0 and 15 min of MCA occlusion, and at 0 and 22 hours of reperfusion.

FIG. 5 clearly shows that the compounds of the present invention when administered during ischemia significantly reduces injury to the cortex. Thus, significant protection of neurons in vivo may be achieved using the compounds of the present invention.

In Vitro Assay of NAALADase Inhibitors on a Cancer Cell Line

Figure 6:
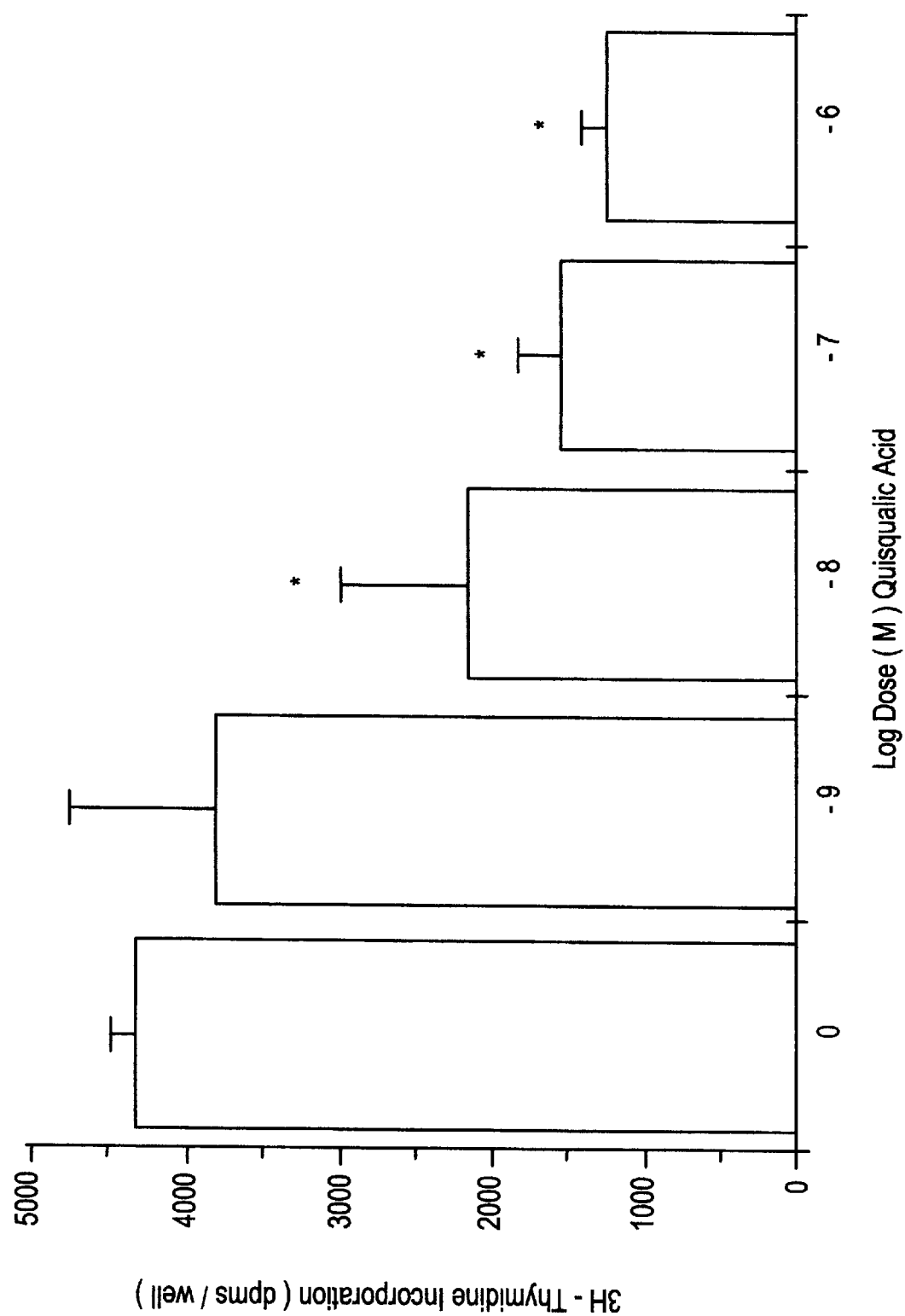
FIG. 6 is a bar graph plotting the growth of the prostate cancer cell line, LNCAP, against various concentrations of quisqualic acid.
Figure 7:
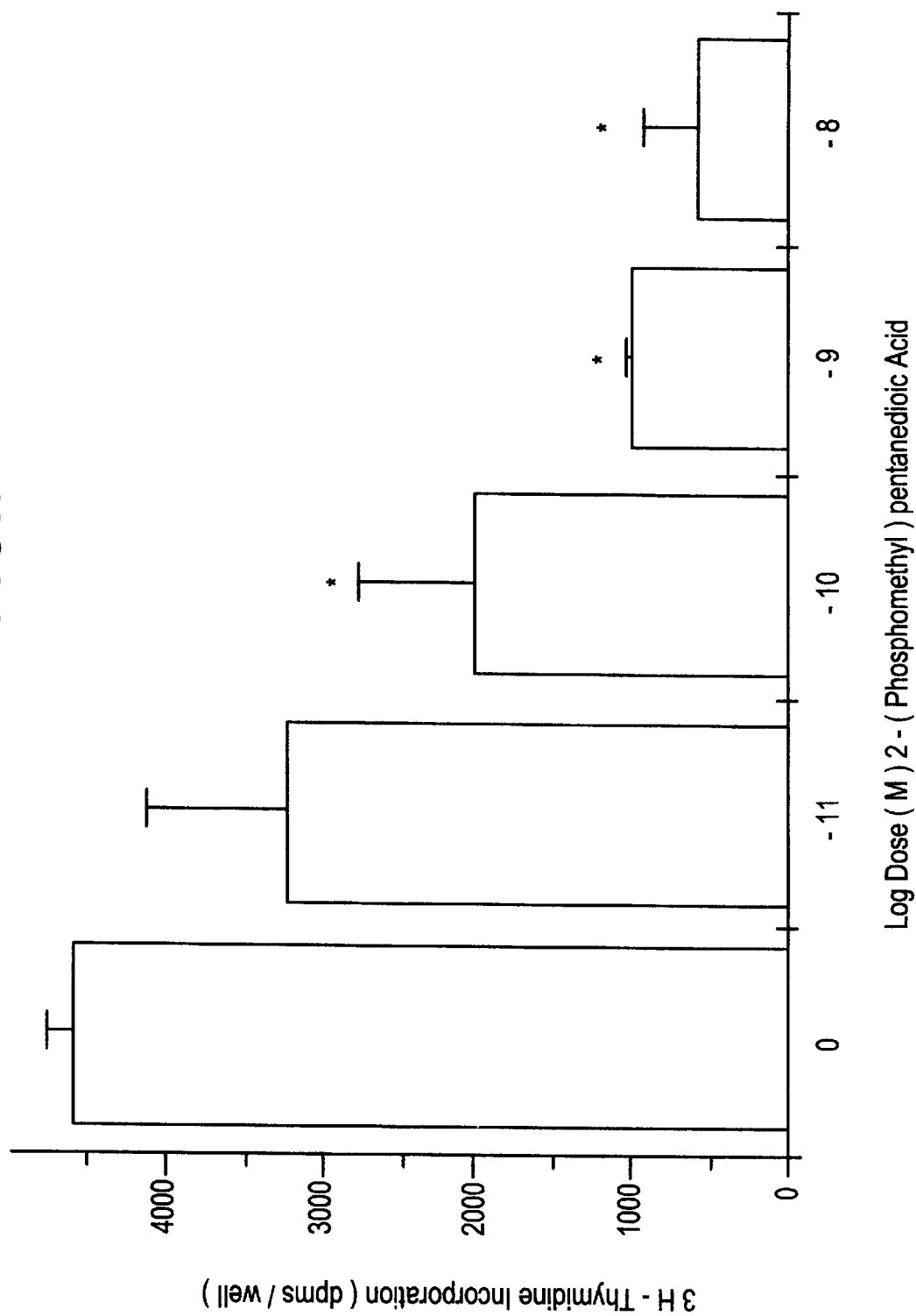
FIG. 7 is a bar graph plotting the growth of the prostate cancer cell line, LNCAP, against various concentrations of 2-(phosphonomethyl)pentanedioic acid.

Referring now to FIGS. 6 and 7 of the drawings, the effect of 7-day treatment with quisqualate and 2-(phosphonomethyl)pentanedioic acid on the growth of LNCAP cells (a prostate cancer cell line) is shown in FIGS. 6 and 7, respectively. Concentrations ranging from 10 nM to 1 μM of quisqualate and 100 pM to 10 nM of 2-(phosphonomethyl)pentanedioic acid show a sharp dose-dependent decrease of LNCAP cell proliferation as indicated by the significant decrease in the incorporation of [3H] thymidine. The data for FIGS. 6 and 7 is shown in Table X, below.

TABLE X $^3$H-Thymidine Incorporation (DPMs)

| Dose | Quisqualic Acid | 2(phosphonomethyl) pentanedioic Acid |
|---|---|---|
| Control | 4813 ± 572 | 4299 ± 887 |
| 10 pM | — | 3078 ± 1006 |
| 100 pM | — | 2062 ± 595 |
| 1 nM | 3668 ± 866 | 1001 ± 52 |
| 10 nM | 2137 ± 764 | 664 ± 366 |
| 100 nM | 1543 ± 312 | — |
| 1 uM | 1295 ± 181 | — |

The data for Table X is obtained according to the following protocol. Cells in RPMI 1640 medium containing 10% Fetal Calf Serum (FCS) are plated in 24 well plates and allowed to adhere for 24 hours before addition of quisqualic acid ($10^{-9}$ to $10^{-6}$) or 2-(phosphonomethyl)pentanedioic acid ($10^{-11}$ to $10^{-8}$) for 7 days. On the 7th day, the cells are pulsed with 3H-Thymidine for 4 hours, harvested and radioactivity measured. Values represent means±SEM of 6 separate cell wells for each treatment. All experiments are performed at least twice.

To control for the non-specific cytostatic effects of these NAALADase inhibitors, the effects of these agents are simultaneously evaluated on the non-NAALADase containing prostate cell line, DU145 (Carter et al., Proc. Natl. Acad. Sci. USA, (93) 749–753; 1996). The effect of 7-day treatment of quisqualate and 2-(phosphonomethyl)pentanedioic acid at concentrations up to $\mu M$ have no significant effect on cell growth. These observations provide evidence that the NAALADase inhibition properties of these agents are uniquely responsible for their cytostatic effects on prostate carcinoma cell lines.

Cell Lines and Tissue Culture

LNCAP cells are obtained from Dr. William Nelson at the Johns Hopkins School of Medicine in Baltimore, Md. DU145 cells are obtained from American Type Culture Collection (Rockville, Md.). Cells are grown in RPMI-1640 media supplemented with 5% heat-inactivated fetal calf serum, 2 mM-glutamine, 100 units/ml penicillin, and 100 $\mu g/ml$ streptomycin (Paragon) in a humidified incubator at 37° C. in a 5% $CO_2$/95% air atmosphere.

[3H] Thymidine Incorporation Assays

The cells are suspended at $1 \times 10^3$ cells/ml in RPMI-1640 media and seeded into 24-well plates at 500 $\mu l$ per well. After 24 hour incubation, various concentrations of quisqualic acid (Sigma) or the potent NAALADase inhibitor 2-(phosphonomethyl)pentanedioic acid (synthesized according to the methods of Jackson et al., J Med Chem 39(2) 619–622) is added to the wells and the plates are returned to the incubator. On days 3, 5, and 7, media and drug are refreshed. On the 8th day following seeding, each well is pulsed with 1 $\mu Ci$ $^3H$-thymidine (New England Nuclear) for 4 hours. Media is then removed and the wells washed 2 times with phosphate buffered saline (pH=7.4). The contents of each well is subsequently solubilized 250 $\mu l$ of 0.2N NaOH and transferred to scintillation vials. Five mls of UltimaGold (Packard) scintillation cocktail is added and radioactivity is quantitated using a Beckman LS6001 scintillation counter.

The purity and/or identity of all synthetic compounds is ascertained by thin layer chromatography, High Pressure Liquid Chromatography (HPLC), mass spectrometry, and elemental analysis. Proton Nuclear Magnetic Resonance (NMR) spectra are obtained using a Bruker spectrometer. Chemical shifts are reported in parts per million relative to tetramethylsilane as internal standard. Analytical thin-layer chromatography (TLC) is conducted on prelayered silica gel GHLF plates (Analtech, Newark, Del.). Visualization of the plates is accomplished by using UV light, phosphomolybdic acid-ethanol, and/or iodoplatinate charring. Flash chromatography is conducted on Kieselgel 60, 230–400 mesh (E. Merck, Darmstadt, West Germany). Solvents are either reagent or HPLC grade. Reactions are run at ambient temperature and under a nitrogen atmosphere unless otherwise noted. Solutions are evaporated under reduced pressure on a Buchi rotary evaporator.

The following examples are illustrative of preferred embodiments of methods of preparation of compounds of the invention and are not to be construed as limiting the invention thereto. Unless otherwise indicated, all percentages are based upon 100% of the final formulations.

EXAMPLE 1

This example demonstrates the preparation of Dibenzyl 2-Methylenepentanedioate using the general method described in Jackson et al., *J. Med Chem.*, 1996, 39, 619–622.

Benzyl acrylate (19.4 g, 120 mmol) was cooled in a two neck 250 ml round bottom flask to approximately 5° C. To this was added dropwise HMPT (2.14 g, 133.1 mmol) at such a rate as to maintain a temperature of 5°–10° C. Once addition was complete the ice/water bath was removed and the mixture allowed to warm to room temperature. Stirring was continued overnight. The clear yellow liquid was added directly to a silica gel column (4 cm*40 cm) and eluted with a gradient (19:1–9:1) solvent system (hexane/EtOAc). The fractions containing the desired material were combined and evaporated to give 1 (10.1 g, 52%) as a clear and colorless liquid. TLC $R_f$ 0.26 (9:1, Hex./EtOAc).

1H-NMR (CDCl3) 7.2–7.3 (m, 10H); 6.15 (s, 1H); 5.55 (s, 1H); 5.12 (s, 2H); 5.08 (s,2H); 2.58–2.68 (m, 2H); 2.48–2.55 (m, 2H).

EXAMPLE 2

This example demonstrates the preparation of Dibenzyl 2-[[Bis(benzyloxy)phosphoryl]methyl]pentanedioate using the general method described in *J. Med Chem.*, 1996, 39, 619–622.

Dibenzyl phosphite (9.5 g, 36 mmol) in 350 ml of dichloromethane was cooled to 0° C. To this stirring solution was added trimethyl aluminum (18.2 ml, 2.0M solution in hexane, 36.4 mmol). After 30 minutes 1 (6.0 g, 37 mmol) in 90 ml of dichloromethane was added dropwise over 10 minutes. The clear and colorless solution was then warmed to room temperature and left to stir overnight. The mixture was then quenched by the slow addition of 5% HCl. After stirring an additional 1.5 hours the lower organic layer was removed and the aqueous layer extracted once with 100 ml of dichloromethane. The organics were combined, dried ($MgSO_4$), and evaporated to give a clear light golden liquid. The liquid was chromatographed on silica gel (4 cm*30 cm) and eluted with a gradient (4:1–1:1) solvent system (Hexane/EtOAc). The fractions containing the desired product were combined and evaporated to yield 2 (7.1 g, 42%) as a clear and colorless liquid. The liquid was then distilled on a Kughleror apparatus at 0.5 mm Hg and 195°–200° C. The distillate was discarded and the remaining light golden oil was chromatographed on silica gel (1:1, Hex./EtOAc) to give 2.9 g of 2 as a clear and colorless oil. TLC $R_f$ 0.5 (1:1, Hex./EtOAc).

1H-NMR ($CDCl_3$) 7.1–7.4 (m, 20H); 5.05 (s, 2H); 4.8–5.03 (m, 6H); 2.8 (1H); 2.22–2.40 (m, 3H); 1.80–2.02 (m, 3H).

EXAMPLE 3

This example demonstrates the preparation of 2-(Phosphonomethyl)pentanedioic Acid (Compound 3) using the general method described in *J. Med Chem.*, 1996, 39, 619–622.

The benzyl pentanedioate 2(2.9 g, 4.9 mmol) was added to a mixture of 20 ml of methanol containing 0.29 g (6mol %) of 10% Pd/C. This mixture was hydrogenated on a Parr hydrogenator at 40 psi for 24 hours, filtered and evaporated to give 3(1.0 g, 90%) as a clear slightly golden viscous oil.

1H-NMR ($D_2O$) 2.6–2.78(m, 1H); 2.25–2.40(m, 2H); 1.75–2.15(m, 4H).

EXAMPLE 4

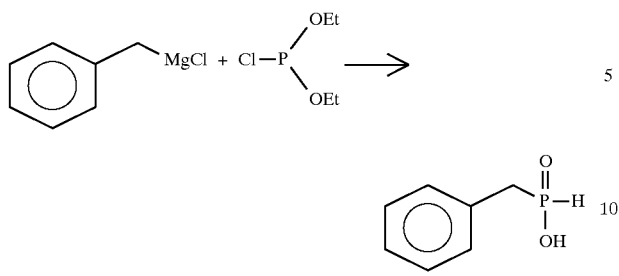

Benzyl magnesium chloride (750 ml of a 1.0M Et$_2$O solution, 0.75 mol) was added dropwise to a cooled (0° C.) stirring solution of diethyl chlorophosphite (110 g, 0.70 mol) in 750 ml of dry ether. Addition was complete after 1.5 hours and the white slurry was warmed to room temperature and left to stir for 16 hours. The mixture was then filtered and the filtrate evaporated under reduced pressure. Water (140 ml) was added followed by a dropwise addition of HCl (10 ml) during which an exothermic was observed. After 30 minutes at room temperature, the solution was extracted with ethyl acetate. The organics were combined and washed with brine, dried (MgSO$_4$), and evaporated to give a clear light yellow liquid. The liquid was then brought up in 80 ml of 10% NaOH and stirred for 1 hour. After this time the mixture was washed with ether and the aqueous layer acidified to pH 1 with concentrated HCl. The solution was then extracted with ethyl acetate. The organics were combined, dried (MgSO$_4$) and evaporated to give 50 g (46%) of a light yellow oil.

EXAMPLE 5

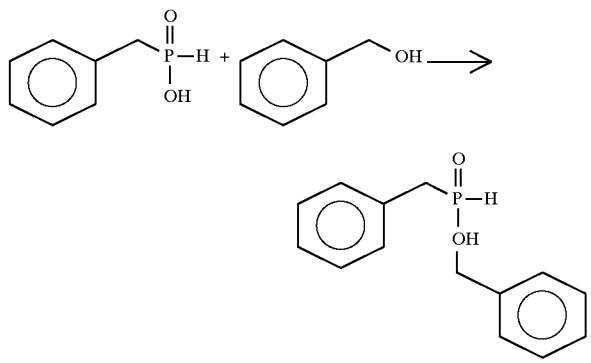

Benzylphosphonous acid (6 g, 38.4 mmol) was added to acetonitrile (25 ml) and cooled to 10° C. Triethylamine (5.4 ml, 38.7 mmol) was added and the temperature maintained at 10° C. Pivaloyl chloride (23.6 ml, 192 mmol) in 50 ml of 1:1 MeCN/Pyridine was added dropwise over 15 minutes. Once addition was complete benzyl alcohol (20 ml, 193 mmol) was added dropwise over 15 minutes. The mixture was warmed to room temperature and stirred for 1 hour. At this time the mixture was acidified with 5% HCl and extracted with dichloromethane. The organics were combined, dried (MgSO$_4$), and evaporated to give a clear liquid. The liquid was purified by flash chromatography and eluted using a 1:1 hexane/EtOAc solvent system. The desired fractions were combined and evaporated under reduced pressure to give 4.5 g of a clear and colorless liquid.

EXAMPLE 6

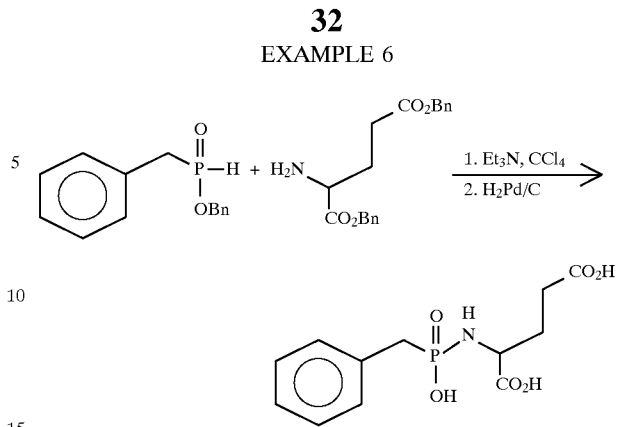

O-Benzyl-benzylphosphonous acid (2 g, 8.1 mmol) was added to carbon tetrachloride (20 ml). Triethylamine (4 ml, 29 mmol) was added dropwise followed by tosyl dibenzyl glutamate (4 g, 8.0 mmol) in 10 ml of carbon tetrachloride. The mixture was stirred for 16 hours and then acidified with 5% HCl. The mixture was then extracted with dichloromethane. The organics were combined, dried (MgSO$_4$), and evaporated to give a clear light yellow liquid. This was purified by flash chromatography to give a clear colorless liquid. The liquid was then hydrogenated at 40 psi in water containing 10% Pd/C. Once hydrogenation was complete (24 hours) the mixture was filtered through Celite and lyophilized to afford N-[(Phenylmethyl)hydroxyphosphinyl] glutamic Acid.

EXAMPLE 7

A patient is at risk of injury from an ischemic event. The patient would then be pretreated with an effective amount of the compounds of the present invention, such as set forth in example 6. It would be expected that after the pretreatment the patient would be protected from the injury.

EXAMPLE 8

A patient is suffering from an ischemic event. The patient may then be administered, during the event or within a 30 minute window after such an event, an effective amount of the compounds of the present invention, such as set forth in example 6. It would be expected that the patient would recover or would not suffer significant injury due to the ischemic event.

EXAMPLE 9

A patient has suffered from an ischemic injury. The patient may then be administered an effective amount of the compounds of the present invention, such as set forth in example 6. It would be expected that the patient would recover from the ischemic injury.

EXAMPLE 10

A patient is suffering from a disease characterized by glutamate abnormality. The patient may then be administered an effective amount of the compounds of the present invention, such as set forth in example 6. It would be expected that the patient would be protected from further injury caused by the glutamate abnormality or would recover from the disease.

EXAMPLE 11

A patient is diagnosed as requiring treatment for glutamate regulation. The patient may then be administered an effective amount of the compounds of the present invention, such as set forth in example 6. It would be expected that the patient's prognosis would improve, the patient would be protected from injury associated with glutamate regulation or the patient would recover from the disease requiring the treatment.

EXAMPLE 12

A patient is suffering from or has suffered a nervous insult, such as that arising from a neurodegenerative disease or neurodegenerative process. The patient may then be administered an effective amount of the compounds of the present invention, such as set forth in example 6. It would be expected that the patient would be protected from further injury or would recover from the nervous insult.

EXAMPLE 13

A patient is suffering from Parkinson's disease. The patient may then be administered an effective amount of the compounds of the present invention, such as set forth in example 6. It would be expected that the patient would be protected from further neurodegeneration or would recover from the disease.

EXAMPLE 14

A patient is suffering from amyotrophic lateral sclerosis. The patient may then be administered an effective amount of the compounds of the present invention, such as set forth in example 6. It would be expected that the patient would be protected from further neurodegeneration or would recover from the disease.

EXAMPLE 15

A patient is suffering from epilepsy. The patient may then be administered an effective amount of the compounds of the present invention, such as set forth in example 6. It would be expected that the patient would be protected from further neurodegeneration or would recover from the disease.

EXAMPLE 16

A patient is suffering from abnormalities in myelination/demyelination processes. The patient may then be administered an effective amount of the compounds of the present invention, such as set forth in example 6. It would be expected that the patient would be protected from further neurodegeneration or would recover from the disease.

EXAMPLE 17

A patient is diagnosed as suffering from a cerebrovascular accident, such as stroke. The patient may then be administered an effective amount of the compounds of the present invention, such as set forth in example 6. It would be expected that after the treatment the patient would be significantly protected from or would recover from injury due to the cerebrovascular accident.

EXAMPLE 18

A patient is diagnosed as suffering from a head trauma. The patient may then be administered an effective amount of the compounds of the present invention, such as set forth in example 6. It would be expected that after the treatment the patient would be significantly protected from or would recover from injury due to an ischemic brain, spinal, or peripheral injury resulting from the head trauma.

EXAMPLE 19

A patient is diagnosed as suffering from a spinal trauma. The patient may then be administered an effective amount of the compounds of the present invention, such as set forth in example 6. It would be expected that after the treatment the patient would be significantly protected from or would recover from ischemic injury resulting from the spinal trauma.

EXAMPLE 20

A patient is going to undergo surgery. The patient may then be administered an effective amount of the compounds of the present invention, such as set forth in example 6. It would be expected that after the treatment the patient would not develop an ischemic brain, spinal, or peripheral injury resulting from or associated with the surgery.

EXAMPLE 21

A patient is diagnosed as suffering from focal ischemia, such as that associated with thromboembolytic occlusion of a cerebral vessel, traumatic head injury, edema or brain tumors. The patient may then be administered an effective amount of the compounds of the present invention, such as set forth in example 6. It would be expected that after the treatment the patient would be significantly protected from or would recover from brain, spinal, or peripheral injury resulting from focal ischemia.

EXAMPLE 22

A patient is diagnosed as suffering from global ischemia. The patient may then be administered an effective amount of the compounds of the present invention, such as set forth in example 6. It would be expected that after the treatment the patient would be significantly protected from or would recover from a brain, spinal, or peripheral injury resulting from global ischemia.

EXAMPLE 23

A patient is diagnosed as suffering from a cardiac arrest. The patient may then be administered the compounds of the present invention, such as set forth in example 6. It would be expected that after the treatment the patient would be significantly protected from or would recover from an ischemic brain, spinal, or peripheral injury associated with cardiac arrest.

EXAMPLE 24

A patient is diagnosed as suffering from hypoxia, asphyxia or perinatal asphyxia. The patient may then be administered the compounds of the present invention, such as set forth in example 6. It would be expected that after the treatment the patient would be significantly protected from or would recover from an ischemic brain, spinal, or peripheral injury associated with the hypoxia, asphyxia or perinatal asphyxia.

EXAMPLE 25

A patient is diagnosed as suffering from a cerebro-cortical injury. The patient may then be administered the compounds of the present invention, such as set forth in example 6. It would be expected that after the treatment the patient would be significantly protected from or would recover from an ischemic brain injury resulting from the cerebro-cortical injury.

EXAMPLE 26

The patient is diagnosed as suffering from an injury to the caudate nucleus. The patient may then be administered the compounds of the present invention, such as set forth in example 6. It would be expected that after the treatment the patient would be significantly protected from or would recover from an ischemic brain injury resulting from the injury to the caudate nucleus.

EXAMPLE 27

A patient is diagnosed with a condition as shown in these examples. The compounds of the present invention may then be administered to the patient intravenously, intramuscularly, intraventricularly to the brain, rectally, subcutaneously, intranasally, through a catheter with or without a pump, placed adjacent or near tissue damaged by an ischemic event, orally, through a transdermal patch and/or topically, or through a polymer implant located adjacent to or near tissue damaged by an ischemic event. The patient's condition would be expected to improve.

EXAMPLE 28

A patient is diagnosed with a condition as shown in these examples. The compounds of the present invention may then be administered to the patient through a 100 mg/kg bolus. This may be followed by a 20 mg/kg intravenous infusion per hour over a two-hour period. The patient's condition would be expected to improve.

EXAMPLE 29

A patient is diagnosed with an cortical injury due to a condition such as set forth in these examples. The patient may then be administered the compounds of the present invention, such as set forth in example 6. It would be expected that the patient would be significantly protected from further injury, or would exhibit at least 65% to at least 80% recovery from the injury after treatment.

EXAMPLE 30

A patient is diagnosed with adenocarcinoma of the prostate. The patient may then be administered a NAALADase inhibitor, such as set forth in example 6, by direct injection into the tumor. After this initial treatment, the patient may be optionally administered the same or different NAALADase inhibitor by intermittent or continuous administration by subdural pump. It would be expected that no further occurrences of the adenocarcinoma would develop.

EXAMPLE 31

A patient is diagnosed with adenocarcinoma of the prostate. The patient may then be administered a NAALADase inhibitor, such as set forth in example 6, by direct injection into the tumor. After this initial treatment, the patient may be optionally administered the same or different NAALADase inhibitor by intermittent or continuous administration by implantation of a biocompatible, polymeric matrix delivery system. It would be expected that no further occurrences of the adenocarcinoma would develop.

EXAMPLE 32

A patient is diagnosed with benign prostatic hyperplasia. The patient may then be administered a NAALADase inhibitor, such as set forth in example 6, by direct injection into the tumor. After this initial treatment, the patient may be optionally administered the same or different NAALADase inhibitor by intermittent or continuous administration by injection, subdural pump, or polymeric matrix implant. It would be expected that the benign prostatic hyperplastic cells do not develop into carcinoma.

EXAMPLE 33

A patient is diagnosed with adenocarcinoma of the prostate. The adenocarcinoma appears not to have metastasized. The adenocarcinoma would be removed by surgery. After post-operative recovery, the patient would be locally administered NAALADase inhibitor by intermittent or continuous administration by injection, subdural pump or by polymeric matrix implant. It would expected that no further occurrences of the carcinoma would develop.

EXAMPLE 34

A patient is diagnosed with metastatic adenocarcinoma of the prostate. The adenocarcinoma appears to have metastasized, but surgery still is indicated as an effective treatment modality. Tumor tissue would be removed by surgery. The patient would be locally administered a NAALADase inhibitor such as described herein from the time, approximately, of the initial diagnosis and would continue after surgery. After post-operative recovery, the patient would be maintained at this level of NAALADase inhibitor by a regimen of periodic local administration. The patient would be monitored carefully for intolerable adverse side-effects of NAALADase inhibitor administration. It would be expected that no further tumors develop. If some of the original, small tumorous masses are detected after surgery, they would be expected to not grow in size.

EXAMPLE 35

A patient is diagnosed with cancer as defined herein. The patient may then be administered a NAALADase inhibitor, such as set forth in example 6, by direct administration to the cancer cells. After this initial treatment, the patient may be optionally administered the same or different NAALADase inhibitor by direct injection, subdural pump, or implantation of a biocompatible, polymeric matrix delivery system. It would be expected that tumor growth or tumor cell growth would be prevented or inhibited and that no further occurrences of the cancer/tumor would develop.

The invention being thus described, it will be obvious that the same may be varied in many ways. Such variations are not to be regarded as a departure from the spirit and scope of the invention and all such modification are intended to be included within the scope of the following claims.

What is claimed is:

1. A compound having the following formula:

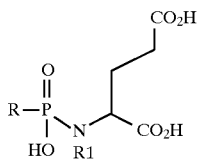

where
R and R1 are independently hydrogen, $C_1$–$C_9$ straight or branched chain alkyl or alkenyl group, $C_3$–$C_8$ cycloalkyl, $C_5$–$C_7$ cycloalkenyl, or $Ar_1$, wherein said alkyl, alkenyl, cycloalkyl, cycloalkenyl or $Ar_1$ groups are optionally substituted with $C_3$–$C_8$ cycloalkyl, $C_3$ or $C_5$ cycloalkyl, $C_5$–$C_7$ cycloalkenyl, $C_1$–$C_4$ alkyl, $C_1$–$C_4$ alkenyl, hydroxy, halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, amino, or $Ar_1$, and where $Ar_1$ is selected from the group consisting of 1-naphthyl, 2-naphthyl, 2-indolyl, 3-indolyl, 2-furyl, 3-furyl, 2-thienyl, 3-thienyl, 2-pyridyl, 3-pyridyl, or 4-pyridyl, and phenyl, said $Ar_1$ having one to three substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, benzyloxy, and amino; or pharmaceutically acceptable salts or hydrates thereof.

2. The compound of claim 1, in combination with an additional therapeutic agent.

3. A pharmaceutical composition for inhibiting N-Acetylated Alpha-Linked Acidic Dipeptidase activity which comprises: (i) an effective amount of the compound of claim 1 and (ii) a suitable pharmaceutical carrier.

4. A method of inhibiting N-Acetylated Alpha-Linked Acidic Dipeptidase enzyme activity which comprises: (i) administering to said enzyme an effective amount of the compound of claim 1 in a pharmaceutically acceptable carrier.

5. A pharmaceutical composition for treating ischemia in an animal which comprises: (i) an effective amount of the compound of claim 1 and (ii) a pharmaceutically acceptable carrier.

6. A method of treating ischemia in an animal which comprises: administering to said animal an effective amount of the compound of claim 1 in a pharmaceutically acceptable carrier.

7. A prostate tumor cell growth inhibiting pharmaceutical composition which comprises: (i) an effective amount of the compound of claim 1 and (ii) a suitable pharmaceutical carrier.

8. A method of inhibiting prostate tumor cell growth which comprises: administering to said tumor cell an effective amount of the compound of claim 1 in a suitable pharmaceutical carrier.

9. The prostate tumor cell growth inhibiting pharmaceutical composition of claim 7, further comprising an additional therapeutic agent selected from the group consisting of therapeutic hormones, chemotherapeutic agents, monoclonal antibodies for cancer therapy, anti-angiogenesis agents, radiolabelled compounds selected from the group consisting of (i) Indium-111 labelled Prostate Specific Membrane Antigen antibody and (ii) monoclonal antibody conjugated with strontium-89, and mixtures thereof.

10. The tumor cell growth inhibiting pharmaceutical composition of claim 7, wherein the tumor is prostatic adenocarcinoma.

11. A pharmaceutical composition for treating prostate diseases selected from the group consisting of prostate cancer and benign prostatic hyperplasia in an animal comprising: (i) an effective amount of the compound of claim 1 and (ii) a suitable pharmaceutical carrier.

12. A method of treating prostate diseases selected from the group consisting of prostate cancer and benign prostatic hyperplasia in an animal comprising: (i) administering an effective amount of the compound of claim 1 in a suitable pharmaceutical carrier.

13. A compound selected from the group consisting of:
N-[Methylhydroxyphosphinyl]glutamic Acid;
N-[Ethylhydroxyphosphinyl]glutamic Acid;
N-[Propylhydroxyphosphinyl]glutamic Acid;
N-[Butylhydroxyphosphinyl]glutamic Acid;
N-[Phenylhydroxyphosphinyl]glutamic Acid;
N-[(Phenylmethyl)hydroxyphosphinyl]glutamic Acid;
N-[((2-Phenylethyl)methyl)hydroxyphosphinyl]glutamic Acid; and
N-Methyl-N-[Phenylhydroxyphosphinyl]glutamic Acid.

14. The compound of claim 13, in combination with an additional therapeutic agent.

15. A pharmaceutical composition for inhibiting N-Acetylated Alpha-Linked Acidic Dipeptidase activity which comprises: (i) an effective amount of the compound of claim 13 and (ii) a suitable pharmaceutical carrier.

16. A method of inhibiting N-Acetylated Alpha-Linked Acidic Dipeptidase enzyme activity which comprises: (i) administering to said enzyme an effective amount of the compound of claim 13 in a pharmaceutically acceptable carrier.

17. A pharmaceutical composition for treating ischemia in an animal which comprises: (i) an effective amount of the compound of claim 13 and (ii) a pharmaceutically acceptable carrier.

18. A method of treating ischemia in an animal which comprises: administering to said animal an effective amount of the compound of claim 13 in a pharmaceutically acceptable carrier.

19. A prostate tumor cell growth inhibiting pharmaceutical composition containing (i) an effective amount of the compound of claim 13 and (ii) a suitable pharmaceutical carrier.

20. A method of inhibiting prostate tumor cell growth which comprises: administering to said tumor cell an effective amount of the compound of claim 13 in a suitable pharmaceutical carrier.

21. The prostate tumor cell growth inhibiting pharmaceutical composition of claim 19, further comprising an additional therapeutic agent selected from the group consisting of therapeutic hormones, chemotherapeutic agents, monoclonal antibodies for cancer therapy, anti-angiogenesis agents, radiolabelled compounds selected from the group consisting of (i) Indium-111 labelled Prostate Specific Membrane Antigen antibody and (ii) monoclonal antibody conjugated with strontium-89, and mixtures thereof.

22. The tumor cell growth inhibiting pharmaceutical composition of claim 19, wherein the tumor is prostatic adenocarcinoma.

23. A pharmaceutical composition for treating prostate diseases selected from the group consisting of prostate cancer and benign prostatic hyperplasia in an animal comprising: (i) an effective amount of the compound of claim 1 and (ii) a suitable pharmaceutical carrier.

24. A method of treating prostate diseases selected from the group consisting of prostate cancer and benign prostatic hyperplasia in an animal comprising: (i) administering an effective amount of the compound of claim 1 in a suitable pharmaceutical carrier.

* * * * *

UNITED STATES PATENT AND TRADEMARK OFFICE
CERTIFICATE OF CORRECTION

PATENT NO. : 5,863,536
DATED : January 26, 1999
INVENTOR(S) : JACKSON et al.

It is certified that error appears in the above-indentified patent and that said Letters Patent is hereby corrected as shown below:

Claim 23, line 55, please remove "claim 1" and replace with -- claim 13 --.

Claim 24, line 60, please remove "claim 1" and replace with - claim 13 -.

Signed and Sealed this

Thirtieth Day of May, 2000

Attest:

Q. TODD DICKINSON

Attesting Officer   Director of Patents and Trademarks